(12) United States Patent
Ferlin et al.

(10) Patent No.: US 8,034,344 B2
(45) Date of Patent: Oct. 11, 2011

(54) ANTI-IL-6/IL-6R ANTIBODIES AND METHODS OF USE THEREOF

(75) Inventors: Walter Ferlin, Saint Cergues (FR); Marie Kosco-Vilbois, Minzier (FR); Greg Elson, Collonges sous Saleve (FR); Olivier Leger, St.-Sixt (FR); Florence Guilhot, Saint Julien en Genevois (FR)

(73) Assignee: NovImmune S.A., Geneva (CH)

( * ) Notice: Subject to any disclaimer, the term of this patent is extended or adjusted under 35 U.S.C. 154(b) by 251 days.

(21) Appl. No.: 12/465,295

(22) Filed: May 13, 2009

(65) Prior Publication Data

US 2011/0002936 A1    Jan. 6, 2011

Related U.S. Application Data

(60) Provisional application No. 61/127,403, filed on May 13, 2008, provisional application No. 61/194,156, filed on Sep. 25, 2008.

(51) Int. Cl.
*A61K 39/395* (2006.01)
*C07K 16/24* (2006.01)
*C07K 16/28* (2006.01)

(52) U.S. Cl. ............... 424/141.1; 424/142.1; 424/143.1; 424/145.1; 530/388.1; 530/388.15; 530/388.22; 530/388.23

(58) Field of Classification Search ........................ None
See application file for complete search history.

(56) References Cited

U.S. PATENT DOCUMENTS

| | | | |
|---|---|---|---|
| 5,618,700 A | 4/1997 | Novick et al. ............... 435/70.21 |
| 5,670,373 A | 9/1997 | Kishimoto ..................... 435/334 |
| 5,817,790 A | 10/1998 | Tsuchiya et al. ............ 536/23.53 |
| 5,888,510 A | 3/1999 | Kishimoto et al. ......... 424/141.1 |
| 5,990,282 A | 11/1999 | Kishimoto ..................... 530/350 |
| 6,083,501 A | 7/2000 | Miyata et al. ............... 424/158.1 |
| 6,261,250 B1 | 7/2001 | Phillips ....................... 424/143.1 |
| 6,410,691 B1 | 6/2002 | Kishimoto ..................... 530/350 |
| 6,419,944 B2 | 7/2002 | Tobinick ........................ 424/422 |
| 6,428,979 B1 | 8/2002 | Kishimoto ................... 435/69.1 |
| 6,723,319 B1 | 4/2004 | Ito et al. ...................... 424/143.1 |
| 2004/0028681 A1 | 2/2004 | Ito et al. ...................... 424/145.1 |
| 2005/0074821 A1 | 4/2005 | Wild et al. ...................... 435/7.2 |
| 2005/0100550 A1 | 5/2005 | Trikha et al. ................ 424/158.1 |
| 2005/0238644 A1 | 10/2005 | Mihara et al. ............... 424/133.1 |
| 2006/0134113 A1 | 6/2006 | Mihara ........................ 424/143.1 |
| 2006/0165696 A1 | 7/2006 | Hideuki ........................ 514/200 |
| 2006/0188502 A1 | 8/2006 | Giles-Komar et al. .... 424/133.1 |
| 2006/0240012 A1 | 10/2006 | Sugimura et al. ........... 424/133.1 |
| 2006/0251653 A1 | 11/2006 | Okuda et al. .................. 514/12 |
| 2006/0257407 A1 | 11/2006 | Chen et al. .................. 424/139.1 |
| 2006/0292147 A1 | 12/2006 | Yoshizaki et al. ........... 435/69.1 |
| 2007/0036785 A1 | 2/2007 | Kishomoto et al. ........ 424/130.1 |
| 2007/0036788 A1 | 2/2007 | Sheriff et al. .................... 514/12 |
| 2007/0098714 A1 | 5/2007 | Nishimoto et al. ......... 424/130.1 |
| 2007/0148169 A1 | 6/2007 | Yoshizaki et al. .......... 424/133.1 |
| 2007/0207153 A1 | 9/2007 | Fujioka et al. .............. 424/141.1 |
| 2007/0243189 A1 | 10/2007 | Yoshizaki et al. .......... 424/130.1 |
| 2007/0280945 A1 | 12/2007 | Stevens et al. .............. 424/145.1 |
| 2007/0292420 A1 | 12/2007 | Giles-Komar et al. ..... 530/388.1 |
| 2008/0124325 A1 | 5/2008 | Hiroaki ....................... 424/145.1 |
| 2008/0145367 A1 | 6/2008 | Bove et al. .................. 424/130.1 |

FOREIGN PATENT DOCUMENTS

| | | |
|---|---|---|
| EP | 0504307 | 1/1994 |
| EP | 0325474 | 5/1995 |
| EP | 0409607 | 10/1996 |
| EP | 0791359 | 8/1997 |
| EP | 1536012 | 6/2005 |
| JP | 4325095 | 11/1992 |
| JP | 10066582 | 3/1998 |
| WO | WO 95/09873 | 4/1995 |
| WO | WO 96/11020 | 4/1996 |
| WO | WO 96/12503 | 5/1996 |
| WO | WO 98/42377 | 10/1998 |
| WO | WO 99/47170 | 9/1999 |
| WO | WO 00/10607 | 3/2000 |
| WO | WO 2006/119115 | 11/2006 |
| WO | WO 2007/066082 | 6/2007 |
| WO | WO 2007/076927 | 7/2007 |
| WO | WO 2007/143168 | 12/2007 |
| WO | WO 2008/019061 | 2/2008 |
| WO | WO 2008/021237 | 2/2008 |
| WO | WO 2008/065378 | 6/2008 |
| WO | WO 2008/065384 | 6/2008 |
| WO | WO 2008/071685 | 6/2008 |

OTHER PUBLICATIONS

Gaillard, et al., "Identification of a Novel Antigenic Structure of the Human Receptor for Interleukin-6 Involved in the Interaction with the Glycoprotein 130 Chain," Immunology, vol. 89(1): 135-141 (1996).

Grube, et al., "Identification of a Regulatory Domain of the Interleukin-6 Receptor," J. Biological Chemistry, vol. 269(32): 20791-797 (1994).

Mizuguchi et al., "Enhanced signal transduction by a directly fused protein of interleukin-6 and its receptor," J Biosci Bioeng., vol. 91(3):299-304 (2001).

Taga et al, "Interleukin-6 triggers the association of its receptor with a possible signal transducer, gp130," Cell, vol. 58(3):573-81 (1989).

U.S. Appl. No. 09/762,550 as deposited on Feb. 9, 2001 with the U.S. Patent and Trademark Office.

*Primary Examiner* — Prema Mertz

(74) *Attorney, Agent, or Firm* — Mintz Levin Cohn Ferris Globsky and Popeo, P.C.; Ivor R. Elrifi

(57) ABSTRACT

This invention provides fully human monoclonal antibodies that recognize the IL-6/IL-6R complex. The invention further provides methods of using such monoclonal antibodies as a therapeutic, diagnostic, and prophylactic.

6 Claims, 8 Drawing Sheets

```
                  D3§
                   →
huIL-6R-D3   QGCGILQ⌐DPPAN┐TVTAVAR┌NPRWLSVTWQDPHSWNSSFYRLRFELRY┌RAERSKIF┐TV  60
mIL-6R-D3    HSLKMVQ⌐DPPAN⌋LVVSAIPG⌊RPRWLKVSWQHPETWDPSYLLQFLRYR⌊RPVWSKEF⌋TVI 60
                  :: ******:  *: . **** *:******..***: . :. : *:. * **** .  :
                        Mutant 1                              Mutant 2 huIL-6R-D3   MVKDL⌐QHHCVIHDAWSGLR┐HVVQLRAQEE┌FGQGE┐WSEWSPEAMGTPWT-ESRSPPAENEV 119
mIL-6R-D3    LLPVA⌋QYQCVIHDA⌋LRGVK⌋HVVQVRGKEE⌊LDLGQ⌋WSEWSPEVTGTPWIAEPRTTPAG-IL 119
                *   *:::*****  :*:  ****:* :*     * :  ********.*.****     *.* :*:
                        Mutant 3        Mutant 4  Mutant 5 huIL-6R-D3   STPMQALTTNKDDDNI⌐FRDSAN┐- 142  (SEQ ID NO: 40)
mIL-6R-D3    WNPTQVSVEDSANHEDQYES⌊STEA⌋ 143  (SEQ ID NO: 41)
                .* *.   .. :.:   . .*: *:

§: D3 is the third domain of IL-6R (Fibronectin II)
```

D.

| Control mAb | Mutant 1 | Mutant 2 | Mutant 3 | Mutant 4 | Mutant 5 |
| NI-1201 WT | Mutant 1 | Mutant 2 | Mutant 3 | Mutant 4 | Mutant 5 |

Human IL-6R →

US 8,034,344 B2

ANTI-IL-6/IL-6R ANTIBODIES AND METHODS OF USE THEREOF

RELATED APPLICATIONS

This application claims the benefit of U.S. Provisional Application No. 61/127,403, filed May 13, 2008, and U.S. Provisional Application No. 61/194,156, filed Sep. 25, 2008, the contents of each of which are hereby incorporated by reference in their entirety.

FIELD OF THE INVENTION

This invention relates generally to the generation of monoclonal antibodies, e.g., fully human monoclonal antibodies, that recognize the IL-6/IL-6R complex, to monoclonal antibodies, e.g., fully human antibodies that recognize both the IL-6/IL-6R complex and IL-6R, and to methods of using the monoclonal antibodies as therapeutics.

BACKGROUND OF THE INVENTION

Interleukin 6 (IL-6) is a potent pleiotropic cytokine that regulates cell growth and differentiation and is also an important mediator of acute inflammatory responses. IL-6 exhibits its action via a receptor complex consisting of a specific IL-6 receptor (IL-6R) and a signal transducing subunit (gp130). Dysregulated IL-6 signaling has been implicated in the pathogenesis of many diseases, such as multiple myeloma, autoimmune diseases and prostate cancer. Accordingly, there exists a need for therapies that neutralize the biological activities of IL-6 and/or IL-6R.

SUMMARY OF THE INVENTION

The present invention provides monoclonal antibodies such as fully human monoclonal antibodies which recognize membrane bound human Interleukin-6 ("IL-6") when complexed with the human IL-6 receptor (i.e., the human IL-6/IL-6R complex ("IL-6Rc") (i.e., IL-6Rc expressed on the cell surface or in soluble form). The antibodies of the invention are capable of modulating, e.g., blocking, inhibiting, reducing, antagonizing, neutralizing or otherwise interfering with IL-6R intracellular signaling via activation of the JAK/STAT pathway and MAPK cascade. Antibodies of the invention also include antibodies that bind soluble IL-6Rc. In addition, antibodies of the invention include antibodies that bind IL-6Rc, wherein they also bind human IL-6R alone (i.e., when not complexed with IL-6).

The problem to be solved by the instant invention is the generation of antibodies that bind the complex formed by IL-6R and IL-6 to thereby prevent the binding of the IL-6/IL-6R complex ("IL-6Rc") to the transmembrane glycoprotein gp130 and subsequent signaling (both cis and trans), which is activated by the IL-6Rc/gp130 signaling complex.

The antibodies of the invention modulate, e.g., block, inhibit, reduce, antagonize, neutralize or otherwise interfere with, the interaction between the IL-6Rc and gp130. Binding of IL-6 and IL-6R to form the IL-6Rc complex allows the IL-6Rc to interact or otherwise associate with gp130, a transmembrane glycoprotein. In particular, binding of IL-6 to IL-6R leads to disulfide-linked homodimerization of gp130 within a cell, which, in turn, leads to the activation of a tyrosine kinase as the first step in signal transduction. In a preferred embodiment, the antibodies of the invention bind to IL-6Rc and block or otherwise inhibit IL-6Rc from interacting with gp130, thereby preventing, partially or completely, the homodimerization of gp130 and subsequent signaling (cis and trans).

Unlike antibodies that bind to IL-6 or IL-6R individually, for example, in the groove where IL-6 binds to IL-6R, the antibodies of the invention do not inhibit or otherwise interfere with the interaction between IL-6 and IL-6R to form the IL-6Rc complex. The antibodies of the invention are, therefore, used at concentrations that are significantly lower than the concentrations needed for antibodies that block or otherwise interfere with the interaction between IL-6R and IL-6, for example, antibodies that compete with IL-6 for binding to IL-6R or vice versa. In some embodiments, the concentration of the antibodies of the invention is 50-100 times lower than the concentration needed for an antibody that blocks or otherwise interferes with the interaction between IL-6 and IL-6R. For antibodies that block or otherwise interfere with the interaction between IL-6 and IL-6R, a large concentration must be used, for example, to treat inflammation, where the levels of IL-6R increase and/or the expression of IL-6 increases. To compete effectively and over a prolonged period with the increased levels of IL-6 and/or IL-6R, these antibodies that block or otherwise interfere with the interaction between IL-6 and IL-6R must be present in large concentrations.

Exemplary monoclonal antibodies of the invention include, for example, the 39B9 VL1 antibody, the 39B9 VL5 antibody, the 12A antibody and the 5C antibody. Alternatively, the monoclonal antibody is an antibody that binds to the same epitope as the 39B9 VL1 antibody, the 39B9 VL5 antibody, the 12A antibody and the 5C antibody. These antibodies are respectively referred to herein as "huIL-6Rc" antibodies. huIL-6Rc antibodies include fully human monoclonal antibodies, as well as humanized monoclonal antibodies and chimeric antibodies. These antibodies show specificity for human IL-6Rc and IL-6R, and they have been shown to modulate, e.g., block, inhibit, reduce, antagonize, neutralize or otherwise interfere with IL-6Rc mediated intracellular signaling (cis and/or trans signaling).

In a preferred embodiment, the fully human antibodies of the invention include (i) the consensus amino acid sequence QQSXSYPLT (SEQ ID NO: 42) in the light chain complementarity determining region 3 (CDR3), where X is N or Q; (ii) the consensus amino acid sequence GIIPX$_1$FX$_2$TTKYAQX$_3$FQG (SEQ ID NO: 43) in the heavy chain complementarity determining region 2 (CDR2), where X$_1$ is L or A, X$_2$ is D or E, and X$_3$ is Q or K; (iii) the consensus amino acid sequence DRDILTDYYPXGGMDV (SEQ ID NO: 44) in the heavy chain complementarity determining region 3 (CDR3), where X is M or L; and (iv) the consensus amino acid sequence TAVXYCAR (SEQ ID NO: 45) in the framework region 3 (FRW3), where X is F or Y.

For example, in one of the preferred embodiments, the huIL-6Rc antibody includes the amino acid sequence QQSNSYPLT (SEQ ID NO: 26) in the light chain CDR3 region, the amino acid sequence GIIPLFDTTKYAQKFQG (SEQ ID NO: 33) in the heavy chain CDR2 region, the amino acid sequence DRDILTDYYPMGGMDV (SEQ ID NO: 36) in the heavy chain CDR3 region, and the amino acid sequence TAVYYCAR (SEQ ID NO: 39) in the FRW3 region. This antibody is referred to herein as the NI-1201A antibody.

In another of the preferred embodiments, the huIL-6Rc antibody includes the amino acid sequence QQSNSYPLT (SEQ ID NO: 26) in the light chain CDR3 region, the amino acid sequence GIIPLFDTTKYAQKFQG (SEQ ID NO: 33) in the heavy chain CDR2 region, the amino acid sequence DRDILTDYYPLGGMDV (SEQ ID NO: 37) in the heavy chain CDR3 region, and the amino acid sequence TAVYY-CAR (SEQ ID NO: 39) in the FRW3 region. This antibody is referred to herein as the NI-1201B antibody.

In another of the preferred embodiments, the huIL-6Rc antibody includes the amino acid sequence QQSNSYPLT (SEQ ID NO: 26) in the light chain CDR3 region, the amino acid sequence GIIPAFETTKYAQKFQG (SEQ ID NO: 34) in the heavy chain CDR2 region, the amino acid sequence DRDILTDYYPLGGMDV (SEQ ID NO: 37) in the heavy chain CDR3 region, and the amino acid sequence TAVYY-CAR (SEQ ID NO: 39) in the FRW3 region. This antibody is referred to herein as the NI-1201C antibody.

In another of the preferred embodiments, the huIL-6Rc antibody includes the amino acid sequence QQSQSYPLT (SEQ ID NO: 32) in the light chain CDR3 region, the amino acid sequence GIIPAFETTKYAQKFQG (SEQ ID NO: 34) in the heavy chain CDR2 region, the amino acid sequence DRDILTDYYPLGGMDV (SEQ ID NO: 37) in the heavy chain CDR3 region, and the amino acid sequence TAVYY-CAR (SEQ ID NO: 39) in the FRW3 region. This antibody is referred to herein as the NI-1201D antibody.

In other embodiments, the huIL-6Rc antibody includes the amino acid sequence QQSNSYPLT (SEQ ID NO: 26) in the light chain CDR3 region, the amino acid sequence GII-PLFDTTKYAQQFQG (SEQ ID NO: 16) in the heavy chain CDR2 region, the amino acid sequence DRDILTDYYPMG-GMDV (SEQ ID NO: 36) in the heavy chain CDR3 region, and the amino acid sequence TAVFYCAR (SEQ ID NO: 38) in the FRW3 region. This antibody is referred to herein as the NI-1201 wild type (NI-1201-WT) antibody.

The fully human antibodies of the invention contain a heavy chain variable region having the amino acid sequence of SEQ ID NOS: 2, 8, and 12. The fully human antibodies of the invention contain a light chain variable region having the amino acid sequence of SEQ ID NOS: 4, 6, 10 and 14. The antibody binds to IL-6R, to IL-6R complexed with IL-6 (i.e., IL-6Rc) or both.

The three heavy chain CDRs include a variable heavy chain (VH) complementarity determining region 1 (CDR1) that includes an amino acid sequence at least 90%, 92%, 95%, 97% 98%, 99% or more identical to a sequence selected from the group consisting of SEQ ID NOs: 15, 18 and 21; a VH complementarity determining region 2 (CDR2) that includes an amino acid sequence at least 90%, 92%, 95%, 97% 98%, 99% or more identical to a sequence selected from the group consisting of SEQ ID NOs: 16, 19, 22, 33, 34 and 35; and a VH complementarity determining region 3 (CDR3) that includes an amino acid sequence at least 90%, 92%, 95%, 97% 98%, 99% or more identical to a sequence selected from the group consisting of SEQ ID NOs: 17, 20, 23, 36 and 37. The antibody binds to IL-6R, to IL-6R complexed with IL-6 (i.e., IL-6Rc) or both.

The three light chain CDRs include variable light chain (VL) CDR1 that includes an amino acid sequence at least 90%, 92%, 95%, 97% 98%, 99% or more identical to a sequence selected from the group consisting of SEQ ID NOs: 24, 27, 28, and 30; a VL CDR2 that includes an amino acid sequence at least 90%, 92%, 95%, 97% 98%, 99% or more identical to the amino acid sequence of SEQ ID NO: 25; and a VL CDR3 that includes an amino acid sequence at least 90%, 92%, 95%, 97% 98%, 99% or more identical to a sequence selected from the group consisting of SEQ ID NOs: 26, 29, 31 and 32. The antibody binds to IL-6R, to IL-6R complexed with IL-6 (i.e., IL-6Rc) or both.

The huIL-6Rc antibodies provided herein are fully human antibodies that bind to IL-6/IL-6R complex (IL-6Rc) and prevent IL-6Rc from binding to gp130 such that gp130-mediated intracellular signaling cascade is not activated in the presence of these antibodies. Preferably, the antibodies have an affinity of at least $1 \times 10^{-8}$ for IL-6Rc, and more preferably, the antibodies have an affinity of at least $1 \times 10^{-9}$ for IL-6Rc.

Antibodies of the invention immunospecifically bind IL-6Rc wherein the antibody binds to an epitope that includes one or more amino acid residues on human IL-6 and/or human IL-6R. Antibodies of the invention immunospecifically binds both IL-6Rc and IL-6R, wherein the antibody binds to an epitope that includes one or more amino acid residues on human IL-6 and/or human IL-6R. Preferably, the huIL-6Rc antibodies described herein bind to an epitope in domain 3 of IL-6 receptor (IL-6R). More preferably, the epitope to which the huIL-6Rc antibodies bind includes at least the amino acid sequence AERSKT (SEQ ID NO: 46).

Antibodies of the invention also include fully human antibodies that specifically bind IL-6Rc, and antibodies that specifically bind both IL-6Rc and IL-6R, wherein the antibody exhibits greater than 50% inhibition of IL-6 mediated activation of the JAK/STAT pathway and MAPK cascade. For example, antibodies of the invention exhibit greater than 55%, 60%, 65%, 70%, 75%, 80%, 85%, 90%, 92%, 95%, 97%, 98%, or 99% inhibition of IL-6 mediated functions including STAT3 activation, acute phase protein production, antibody production and cellular differentiation and/or proliferation.

The present invention also provides methods of treating or preventing pathologies associated with aberrant IL-6 receptor activation and/or aberrant IL-6 signaling (cis and/or trans) or alleviating a symptom associated with such pathologies, by administering a monoclonal antibody of the invention (e.g., fully human monoclonal antibody) to a subject in which such treatment or prevention is desired. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce IL-6Rc induced activation of the JAK/STAT pathway or MAPK cascade. For example, IL-6Rc induced activation of the JAK/STAT pathway or MAPK cascade is decreased when the level of STAT3 activation in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of STAT3 activation (i.e., the level of STAT3 activation in the absence of the monoclonal antibody). Those skilled in the art will appreciate that the level of STAT3 activation can be measured using a variety of assays, including, for example, commercially available ELISA kits.

Pathologies treated and/or prevented using the monoclonal antibodies of the invention (e.g., fully human monoclonal antibody) include, for example, sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus).

Pharmaceutical compositions according to the invention can include an antibody of the invention and a carrier. These pharmaceutical compositions can be included in kits, such as, for example, diagnostic kits.

One skilled in the art will appreciate that the antibodies of the invention have a variety of uses. For example, the proteins of the invention are used as therapeutic agents to prevent IL-6 receptor activation in disorders such as, for example, sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus). The antibodies of the invention are also used as reagents in diagnostic kits or as diagnostic tools, or these antibodies can be used in competition assays to generate therapeutic reagents.

DETAILED DESCRIPTION

Figure 1:
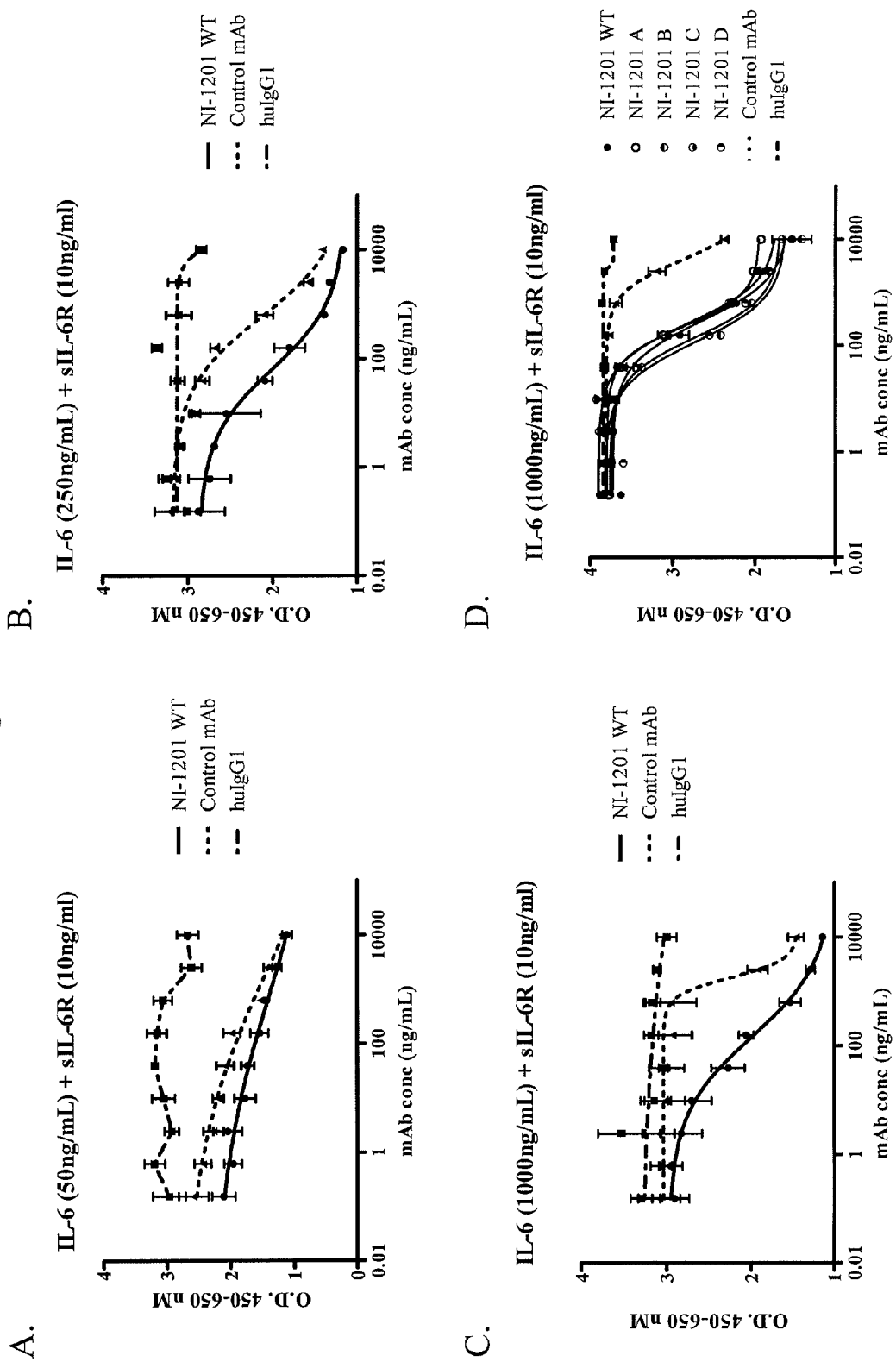
FIGS. 1A-1D are a series of graphs depicting the ability of an antibody of the invention, NI-1201, to block IL-6 trans-signaling.

The present invention provides monoclonal antibodies that specifically bind the human IL-6/IL-6 receptor complex ("IL-6Rc"), in soluble form, or membrane bound (i.e., when expressed on a cell surface). The invention further provides monoclonal antibodies that specifically bind IL-6Rc, wherein the antibodies also bind IL-6R when not complexed with IL-6. These antibodies are collectively referred to herein as "huIL-6Rc" antibodies. The antibody is e.g., a fully human antibody.

Antibodies of the invention specifically bind IL-6Rc and/or both IL-6Rc and IL-6R wherein the antibody binds to an epitope that includes one or more amino acid residues of human IL-6, IL-6R, or both.

The antibodies of the present invention bind to an IL-6Rc and/or both IL-6Rc and IL-6R epitope with an equilibrium binding constant ($K_d$) of $\leq 1$ μM, e.g., $\leq 100$ nM, preferably $\leq 10$ nM, and more preferably $\leq 1$ nM. For example, the huIL-6Rc antibodies provided herein exhibit a $K_d$ in the range approximately between $\leq 1$ nM to about 1 pM.

IL-6 acts as both a pro-inflammatory and anti-inflammatory cytokine. It is secreted by T cells and macrophages to stimulate immune response to trauma, especially burns or other tissue damage leading to inflammation. IL-6 is one of the most important mediators of fever and of the acute phase response. In the muscle and fatty tissue IL-6 stimulates energy mobilization which leads to increased body temperature. IL-6 can be secreted by macrophages in response to specific microbial molecules, referred to as pathogen associated molecular patterns (PAMPs). These PAMPs bind to highly important detection molecules of the innate immune system, called Toll-like receptors (TLRs), that are present on the cell surface (or in intracellular compartments) which induce intracellular signaling cascades that give rise to inflammatory cytokine production. IL-6 is also essential for hybridoma growth and is found in many supplemental cloning media such as briclone.

IL-6 signals through a cell-surface type I cytokine receptor complex consisting of the ligand-binding IL-6Rα chain (also called known as CD126), and the signal-transducing component gp130 (also called CD130). gp130 is the common signal transducer for several cytokines including leukemia inhibitory factor (LIF), ciliary neurotrophic factor, oncostatin M, IL-11 and cardiotrophin-1, and is almost ubiquitously expressed in most tissues. In contrast, the expression of CD126 is restricted to certain tissues. As IL-6 interacts with its receptor, it triggers the gp130 and IL-6R proteins to form a complex, thus activating the receptor. These complexes bring together the intracellular regions of gp130 to initiate a signal transduction cascade through certain transcription factors, Janus kinases (JAKs) and Signal Transducers and Activators of Transcription (STATs). Accordingly, neutralization of IL-6 signaling is a potential therapeutic strategy in the treatment of disorders such as, for example, sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus).

The huIL-6Rc antibodies of the invention serve to modulate, block, inhibit, reduce, antagonize, neutralize or otherwise interfere with the functional activity of IL-6Rc. Functional activities of IL-6Rc include for example, intracellular signaling via activation of the JAK/STAT pathway and activation of the MAPK cascade, acute phase protein production, antibody production and cellular differentiation and/or proliferation. For example, the huIL-6Rc antibodies completely or partially inhibit IL-6Rc functional activity by partially or completely modulating, blocking, inhibiting, reducing antagonizing, neutralizing, or otherwise interfering with the binding of IL-6Rc to the signal-transducing receptor component gp130.

The huIL-6Rc antibodies are considered to completely modulate, block, inhibit, reduce, antagonize, neutralize or otherwise interfere with IL-6Rc functional activity when the level of IL-6Rc functional activity in the presence of the huIL-6Rc antibody is decreased by at least 95%, e.g., by 96%, 97%, 98%, 99% or 100% as compared to the level of IL-6Rc functional activity in the absence of binding with a huIL-6Rc antibody described herein. The huIL-6Rc antibodies are considered to partially modulate, block, inhibit, reduce, antagonize, neutralize or otherwise interfere with IL-6Rc functional activity when the level of IL-6Rc activity in the presence of the huIL-6Rc antibody is decreased by less than 95%, e.g., 10%, 20%, 25%, 30%, 40%, 50%, 60%, 75%, 80%, 85% or 90% as compared to the level of IL-6Rc activity in the absence of binding with a huIL-6Rc antibody described herein.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms Interleukin-6 Receptor, IL-6R, Interleukin-6 Receptor-alpha, IL-6Rα, cluster differentiation factor 126, and CD126 are synonymous and may be used interchangeably. Each of these terms refers to the homodimeric protein, except where otherwise indicated.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ μM; e.g., $\leq 100$ nM, preferably $\leq 10$ nM and more preferably $\leq 1$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to IL-6Rc and/or both IL-6Rc and IL-6R, when the equilibrium binding constant ($K_d$) is $\leq 1$ μM, preferably $\leq 100$ nM, more preferably $\leq 10$ nM, and most preferably $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules presented in SEQ ID NOS: 2, 8 and 12, and nucleic acid molecules encoding the light chain immunoglobulin molecules represented in SEQ ID NOS: 4, 6, 10, and 14.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 2, 8, and 12, and the light chain immunoglobulin molecules represented in SEQ ID NOS: 4, 6, 10, and 14 as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred.

Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to IL-6Rc and/or both IL-6Rc and IL-6R, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, chronic obstructive pulmonary disease, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Cancers include, for example, multiple myeloma disease (MM), renal cell carcinoma (RCC), plasma cell leukaemia, lymphoma, B-lymphoproliferative disorder (BLPD), and prostate cancer.

huIL-6Rc Antibodies

Monoclonal antibodies of the invention (e.g., fully human monoclonal antibodies) have the ability to inhibit IL-6Rc mediated cell signaling. Inhibition is determined, for example, using the cellular assay described herein in Example 1 and 2.

Exemplary antibodies of the invention include, for example, the 39B9 VL1 antibody, the 39B9 VL5 antibody, the 12A antibody, and the 5C antibody. These antibodies show specificity for human IL-6Rc and/or both IL-6Rc and IL-6R and they have been shown to inhibit the functional activity of IL-6Rc (i.e., binding to gp130 to induce the signaling cascade) in vitro.

Each of the huIL-6Rc monoclonal antibodies described herein includes a heavy chain variable region (VH) and a light chain variable region (VL), as shown in the amino acid and corresponding nucleic acid sequences listed below.

The 39B9 VL1 and 39B9 VL5 antibodies share a common heavy chain variable region (SEQ ID NO:2) encoded by the nucleic acid sequence shown in SEQ ID NO:1

>39B9 VL1-VH nucleic acid sequence
(SEQ ID NO: 1)
5' CAGGTGCAGCTGGTGCAGTCTGGGGCTGAGGTGAAGAAGCCTGGGTCC

TCGGTGAAGGTCTCCTGCAAGGCTTCTGGAGGCACCTTCAGCAGCTATGC

TATCAGCTGGGTGCGCCAGGCCCCTGGACAAGGGCTTGAGTGGATGGGAG

GGATCATCCCTCTCTTTGATACAACAAAGTACGCACAGCAGTTCCAGGGC

AGAGTCACGATTACCGCGGACGAATCCACGAGCACAGCCTACATGGAGCT

GAGCAGCCTGAGATCTGAGGACACGGCCGTATTTTACTGTGCGAGAGATC

GGGATATTTTGACTGATTATTATCCCATGGGCGGTATGGACGTCTGGGGC

CAAGGGACCACGGTCACCGTCTCCTCA 3'

>39B9 VL1-VH amino acid sequence
(SEQ ID NO: 2)
QVQLVQSGAEVKKPGSSVKVSCKASGGTFSSYAISWVRQAPGQGLEWMGG

IIPLFDTTKYAQQFQGRVTITADESTSTAYMELSSLRSEDTAVFYCARDR

DILTDYYPMGGMDVWGQGTTVTVSS

The 39B9 VL1 antibody includes a light chain variable region (SEQ ID NO:4) encoded by the nucleic acid sequence shown in SEQ ID NO:3.

>39B9 VL1-VL nucleic acid sequence
(SEQ ID NO: 3)
5'GCCATCCAGTTGACCCAGTCTCCATCCTCCCTGTCTGCATCTGTAGGA

GACAGAGTCACCATCACTTGCCGGGCAAGTCAGGGCATTAGCAGTGTTTT

AGCCTGGTATCAGCAGAAACCAGGGAAAGCTCCTAAGCTCCTGATCTATG

ATGCCTCCAGTTTGGAAAGTGGGGTCCCATCAAGGTTCAGCGGCAGTGGA

TCTGGGACAGATTTCACTCTCACCATCAGCAGCCTGCAGCCTGAAGATTT

TGCAACTTATTACTGTCAACAGTCTAATAGTTACCCGCTCACTTTCGGCG

GAGGGACCAAGGTGGAGATCAAACGT 3'

>39B9 VL1-VL amino acid sequence
(SEQ ID NO: 4)
AIQLTQSPSSLSASVGDRVTITCRASQGISSVLAWYQQKPGKAPKLLIYD

ASSLESGVPSRFSGSGSGTDFTLTISSLQPEDFATYYCQQSNSYPLTFGG

GTKVEIKR

The 39B9 VL5 antibody includes a light chain variable region (SEQ ID NO:6) encoded by the nucleic acid sequence shown in SEQ ID NO:5.

>39B9 VL5-VL nucleic acid sequence
(SEQ ID NO: 5)
5'GACATCCTGATGACCCAGTCTCCATCCTCCCTGTCTGCATCTGTAGGA

GACAGAGTCACCATCACTTGTCGGGCGAGTCAGGATATTAGCAGCTGGTT

AGCCTGGTATCAGCAGAAACCAGGGAAAGCTCCTAAGCTCCTGATCTATG

ATGCCTCCAGTTTGGAAAGTGGGGTCCCATCAAGGTTCAGCGGCAGTGGA

TCTGGGACAGATTTCACTCTCACCATCAGCAGCCTGCAGCCTGAAGATTT

TGCAACTTATTACTGTCAACAGTCTAATAGTTACCCGCTCACTTTCGGCG

GAGGGACCAAGGTGGAGATCAAACGA 3'

>39B9 VL5-VL amino acid sequence
(SEQ ID NO: 6)
DILMTQSPSSLSASVGDRVTITCRASQDISSWLAWYQQKPGKAPKLLIYD

ASSLESGVPSRFSGSGSGTDFTLTISSLQPEDFATYYCQQSNSYPLTFGG

GTKVEIKR

The 12A antibody includes a heavy chain variable region (SEQ ID NO:8) encoded by the nucleic acid sequence shown in SEQ ID NO:7.

>12A VH nucleic acid sequence
(SEQ ID NO: 7)
5'CAGGTGCAGCTGGTGGAGTCTTGGGGAGGCGTGGTCCAGCCTGGGAGG

TCCCTGAGACTCTCCTGTGCAGCGTCTGGATTCACCTTCAGTAACTATGA

CATGTACTGGGTCCGCCAGGCTCCAGGCAAGGGGCTGGAGTGGGTGGCAG

TTATATTAGATGATGGAAATAATAATTACTACGCAGACTCCGTGAAGGGC

CGATTCACCATCTCCAGAGACAATTCCAAGAAAAAGGTGTATCTGCAAAT

GAATAGCCTGAGAGCTGAGGACACGGCTGTGTATTACTGTGTGAGAGCGT

CCCCTAACTGGGGTCTTCTTGACTTCTGGGGCCAGGGAACCCTGGTCACC

GTCTCGAGT 3'

>12A VH amino acid sequence
(SEQ ID NO: 8)
QVQLVESWGGVVQPGRSLRLSCAASGFTFSNYDMYWVRQAPGKGLEWVAV

ILDDGNNNYYADSVKGRFTISRDNSKKKVYLQMNSLRAEDTAVYYCVRAS

PNWGLLDFWGQGTLVTVSS

The 12A antibody includes a light chain variable region (SEQ ID NO:10) encoded by the nucleic acid sequence shown in SEQ ID NO:9.

>12A VL nucleic acid sequence
(SEQ ID NO: 9)
5'GAAATTGTGTTGACACAGTCTCCATCCTCACTGTCTGCATCTGTAGGA

GACAGAGTCACCATCACTTGTCGGGCGAGTCAGGGTATTAGCAGCTGGTT

AGCCTGGTATCAGCAGAAACCAGGGAAAGCTCCTAAGCTCCTGATCTATG

ATGCCTCCAGTTTGGAAAGTGGGGTCCCATCAAGGTTCAGCGGCAGTGGA

TCTGGGACAGATTTCACTCTCACCATCAGCAGCCTGCAGCCTGAAGATTT

TGCAACTTATTACTGTCAACAGTTTAATAGTTACCCGATCACCTTCGGCC

AAGGGACACGACTGGAGATTAAACGT 3'

>12A VL amino acid sequence
(SEQ ID NO: 10)
EIVLTQSPSSLSASVGDRVTITCRASQGISSWLAWYQQKPGKAPKLLIYD

ASSLESGVPSRFSGSGSGTDFTLTISSLQPEDFATYYCQQFNSYPITFGQ

GTRLEIKR

The 5C antibody includes a heavy chain variable region (SEQ ID NO:12) encoded by the nucleic acid sequence shown in SEQ ID NO:11

>5C VH nucleic acid sequence
(SEQ ID NO: 11)
CAGGTGCAGCTGGTGCAGTCTGGGGGAGGCGTGGTCCAGCCTGGGAGGTC

CCTGAGACTCTCCTGTGCAGCCTCTGGATTCATCTTCAGTAGCTATGACA

TGTACTGGGTCCGCCAGGCTCCAGGCAAGGGGCTGGAGTGGGTGGCAGTT

ATATTATATGATGGAAATAATAAATACTACGCAGACTCCGTGAAGGGCCG

ATTCACCATCTCCAGAGACAATTCCAAGAACACGGTGTATCTGCAAATGA

ACAGCCTGAGAGCTGAGGACACGGCTGTGTATTACTGTGTGAGAGCGTCC

CCTAACTGGGGTCTTTTTGACTTCTGGGGCCAGGGAACCCTGGTCACCGT

CTCGAGT 3'

>5C VH amino acid sequence
(SEQ ID NO: 12)
QVQLVQSGGGVVQPGRSLRLSCAASGFIFSSYDMYWVRQAPGKGLEWVAV

ILYDGNNKYYADSVKGRFTISRDNSKNTVYLQMNSLRAEDTAVYYCVRAS

PNWGLFDFWGQGTLVTVSS

The 5C antibody includes a light chain variable region (SEQ ID NO:14) encoded by the nucleic acid sequence shown in SEQ ID NO:13.

>5C VL nucleic acid sequence
(SEQ ID NO: 13)
5'GACATCCAGATGACCCAGTCTCCATCCTCCCTGTCTGCATCTGTAGGA

GACAGAGTCACCATCACTTGCCGGGCAAGTCAGGGCATTAGCAGTGATTT

AGCCTGGTATCAGCAGAAACCAGGGAAAGCTCCTAAGCTCCTGATGTATG

ATGCCTCCAGTTTGGAAAGTGGGGTCCCATCAAGGTTCAGCGGCAGTGGA

TCTGGGACAGATTTCACTCTCACCATCAGCAGCCTGCAGCCTGAAGATTT

TGCAACTTATTACTGTCAACAGTTTAATAGTTACCCGATCACCTTCGGCC

AAGGGACACGACTGGAGATTAAACGT 3'

>5C VL amino acid sequence
(SEQ ID NO: 14)
DIQMTQSPSSLSASVGDRVTITCRASQGISSDLAWYQQKPGKAPKLLMYD

ASSLESGVPSRFSGSGSGTDFTLTISSLQPEDFATYYCQQFNSYPITFGQ

GTRLEIKR huIL-6Rc antibodies of the invention additionally comprise, for example, the heavy chain complementarity determining regions (VH CDRs) shown below in Table 1, the light chain complementarity determining regions (VL CDRs) shown in Table 2, and combinations thereof.

TABLE 1

VH CDR sequences from antibody clones that bind and neutralize IL-6Rc biological activity

| Clone Name | VH CDR1 | VH CDR2 | VH CDR3 |
|---|---|---|---|
| 39B9 | SYAIS (SEQ ID NO: 15) | GIIPLFDTTKYAQQFQG (SEQ ID NO: 16) | CAR DRDILTDYYPMGGMDV (SEQ ID NO: 17) |
| 12A | NYDMY (SEQ ID NO: 18) | VILDDGNNNYYADSVKG (SEQ ID NO: 19) | CVR ASPNWGLLDF (SEQ ID NO: 20) |
| 5C | SYDMY (SEQ ID NO: 21) | VILYDGNNKYYADSVKG (SEQ ID NO: 22) | CVR ASPNWGLFDF (SEQ ID NO: 23) |

TABLE 2

VL CDR sequences from antibody clones that bind and neutralize IL-6Rc

| Clone Name | VL CDR1 | VL CDR2 | VL CDR3 |
|---|---|---|---|
| 39B9 VL1 | RASQGISSVLA (SEQ ID NO: 24) | DASSLES (SEQ ID NO: 25) | QQSNSYP LT (SEQ ID NO: 26) |
| 39B9 VL5 | RASQDISSWLA (SEQ ID NO: 27) | DASSLES (SEQ ID NO: 25) | QQSNSYP LT (SEQ ID NO: 26) |
| 12A | RASQGISSWLA (SEQ ID NO: 28) | DASSLES (SEQ ID NO: 25) | QQSNSYP IT (SEQ ID NO: 29) |
| 5C | RASQGISSVDA (SEQ ID NO: 30) | DASSLES (SEQ ID NO: 25) | QQSNSYP IT (SEQ ID NO: 31) |

The amino acids encompassing the complementarity determining regions (CDR) are as defined by E. A. Kabat et al. (See Kabat, E A, et al., Sequences of Protein of immunological interest, Fifth Edition, US Department of Health and Human Services, US Government Printing Office (1991)).

Also included in the invention are antibodies that bind to the same epitope as the antibodies described herein. For example, antibodies of the invention specifically bind to IL-6R, wherein the antibody binds to an epitope that includes one or more amino acid residues on human IL-6R (e.g., GenBank Accession No. P08887). Antibodies of the invention specifically bind IL-6Rc, wherein the antibody binds to an epitope that includes one or more amino acid residues on human IL-6 (e.g., GenBank Accession No. NP_000591), IL-6R (e.g., GenBank Accession No. P08887), or both.

Those skilled in the art will recognize that it is possible to determine, without undue experimentation, if a monoclonal antibody (e.g., fully human monoclonal antibody) has the same specificity as a monoclonal antibody of the invention (e.g., clones 39B9 VL1, 39B9 VL5, 12A and 5C) by ascertaining whether the former prevents the latter from binding to gp130. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of monoclonal antibody of the invention is to pre-incubate the monoclonal antibody of the invention with soluble IL-6Rc or IL-6R protein (with which it is normally reactive), and then add the monoclonal antibody being tested to determine if the monoclonal antibody being tested is inhibited in its ability to bind IL-6Rc and/or both IL-6Rc and IL-6R. If the monoclonal antibody being tested is inhibited then, in all likelihood, it has the same, or functionally equivalent, epitopic specificity as the monoclonal antibody of the invention.

Screening of monoclonal antibodies of the invention, can be also carried out, e.g., by measuring IL-6 receptor mediated activation of the JAK/STAT pathways and/or MAPK signaling cascade, and determining whether the test monoclonal antibody is able to modulate, block, inhibit, reduce, antagonize, neutralize or otherwise interfere with IL-6 signaling.

Various procedures known within the art may be used for the production of monoclonal antibodies directed against IL-6Rc and/or both IL-6Rc and IL-6R, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985

In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies of the invention (e.g., 39B9 VL1, 39B9 VL5, 12A and 5C) are fully human monoclonal antibodies. Monoclonal antibodies that modulate, block, inhibit, reduce, antagonize, neutralize or otherwise interfere with IL-6Rc mediated cell signaling are generated, e.g., by immunizing an animal with membrane bound and/or soluble IL-6Rc, such as, for example, murine, rat or human IL-6Rc or an immunogenic fragment, derivative or variant thereof. Alternatively, the animal is immunized with cells transfected with a vector containing a nucleic acid molecule encoding IL-6Rc such that IL-6Rc is expressed and associated with the surface of the transfected cells. Alternatively, the antibodies are obtained by screening a library that contains antibody or antigen binding domain sequences for binding to IL-6Rc. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to IL-6Rc and/or both IL-6Rc and IL-6R.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816, 567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Human Antibodies and Humanization of Antibodies

Monoclonal antibodies of the invention include fully human antibodies or humanized antibodies. These antibodies are suitable for administration to humans without engendering an immune response by the human against the administered immunoglobulin.

A huIL-6Rc antibody is generated, for example, using the procedures described in the Examples provided below.

In other, alternative methods, a huIL-6Rc antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of IL-6Rc or fragments thereof. In another approach, a huIL-6Rc antibody can be produced by a process wherein at least one step of the process includes immunizing a transgenic, non-human animal with human IL-6Rc protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. Nos. 6,075,181 and 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2 and European Patent No., EP 0 463 151 B1 and International Patent Applications Nos. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against IL-6Rc and/or both IL-6Rc and IL-6R in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693, 761; 5,693,792; 5,714,350; and 5,777,085). Also, the use of 1 g cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al.

Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to IL-6Rc expressing cells, soluble forms of IL-6Rc, epitopes or peptides thereof, and expression libraries thereto (See e.g., U.S. Pat. No. 5,703,057) which can thereafter be screened as described above for the activities described herein.

The huIL-6Rc antibodies of the invention can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of IL-6Rc and/or IL-6R in a sample. The antibody can also be used to try to bind to and disrupt IL-6Rc-related signaling.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_{(ab')2}$ fragments.

The invention also includes $F_v$, $F_{ab}$, $F_{ab'}$ and $F_{(ab')2}$ anti-IL-6R fragments or anti-IL-6Rc complex fragments, single chain anti-IL-6R or anti-IL-6Rc antibodies, bispecific anti-IL-6R, and/or anti-IL-6Rc antibodies, and heteroconjugate anti-IL-6R and/or anti-IL-6Rc antibodies.

Bispecific antibodies are antibodies that have binding specificities for at least two different antigens. In the present case, one of the binding specificities is for IL-6Rc or IL-6R. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant IL-6 signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomo-* nas aeruginosa), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against IL-6Rc

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, antibodies of the invention, which include a monoclonal antibody of the invention (e.g., a fully human monoclonal antibody), may be used as therapeutic agents. Such agents will generally be employed to diagnose, prognose, monitor, treat, alleviate, and/or prevent a disease or pathology associated with aberrant IL-6 signaling in a subject. A therapeutic regimen is carried out by identifying a subject, e.g., a human patient suffering from (or at risk of developing) a disease or disorder associated with aberrant IL-6 signaling, e.g., an inflammatory disorder such as rheumatoid arthritis, using standard methods. An antibody preparation, preferably one having high specificity and high affinity for its target antigen, is administered to the subject and will generally have an effect due to its binding with the target. Administration of the antibody may abrogate or inhibit or interfere with the signaling function of the target (e.g., IL-6Rc). Administration of the antibody may abrogate or inhibit or interfere with the binding of the target (e.g., IL-6Rc) with an endogenous ligand (e.g., gp130) to which it naturally binds. For example, the antibody binds to the target and modulates, blocks, inhibits, reduces, antagonizes, neutralizes, or otherwise interferes with IL-6 signaling.

Diseases or disorders related to aberrant IL-6 signaling include sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus).

Symptoms associated with inflammatory-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation. Symptoms associated with immune-related disorders include, for example, inflammation, fever, loss of appetite, weight loss, abdominal symptoms such as, for example, abdominal pain, diarrhea or constipation, joint pain or aches (arthralgia), fatigue, rash, anemia, extreme sensitivity to cold (Raynaud's phenomenon), muscle weakness, muscle fatigue, changes in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular inflammatory-related disorder. Alleviation of one or more symptoms of the inflammatory-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

In another embodiment, antibodies directed against IL-6Rc and/or both IL-6Rc and IL-6R may be used in methods known within the art relating to the localization and/or quantitation of IL-6Rc (e.g., for use in measuring levels of IL-6Rc and/or both IL-6Rc and IL-6R within appropriate physiological samples, for use in diagnostic methods, for use in imaging the protein, and the like). In a given embodiment, antibodies specific to IL-6Rc and/or both IL-6Rc and IL-6R, or derivative, fragment, analog or homolog thereof, that contain the antibody derived antigen binding domain, are utilized as pharmacologically active compounds (referred to hereinafter as "Therapeutics").

In another embodiment, an antibody specific for IL-6Rc can be used to isolate an IL-6R, IL-6Rc, and/or IL-6 polypeptide, by standard techniques, such as immunoaffinity, chromatography or immunoprecipitation. Antibodies directed against the IL-6Rc and/or both IL-6Rc and IL-6R protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In yet another embodiment, an antibody according to the invention can be used as an agent for detecting the presence of IL-6Rc and/or both IL-6Rc and IL-6R protein (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Therapeutic Administration and Formulations of huIL-6Rc Antibodies

The antibodies of the invention (also referred to herein as "active compounds"), and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Such combination therapies may advantageously utilize lower dosages of the administered therapeutic agents, thus avoiding possible toxicities or complications associated with the various monotherapies.

Preferred therapeutic agents used in combination with an antibody of the invention are those agents that interfere at different stages in an inflammatory response. In one embodiment, one or more antibodies described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof.

In other embodiments, the antibodies of the invention are used as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Design and Generation of Other Therapeutics

In accordance with the present invention and based on the activity of the antibodies that are produced and characterized herein with respect to IL-6Rc, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies—one with a specificity to IL-6Rc and/or both IL-6Rc and IL-6R and another to a second molecule that are conjugated together, (ii) a single antibody that has one chain specific to IL-6Rc and/or both IL-6Rc and IL-6R and a second chain specific to a second molecule, or (iii) a single chain antibody that has specificity to IL-6Rc and/or both IL-6Rc and IL-6R and a second molecule. Such bispecific antibodies are generated using techniques that are well known for example, in connection with (i) and (ii) See e.g., Fanger et al. Immunol Methods 4:72-81 (1994) and Wright et al. Crit. Reviews in Immunol. 12125-168 (1992), and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing IL-6Rc.

In connection with the generation of therapeutic peptides, through the utilization of structural information related to IL-6Rc and/or both IL-6Rc and IL-6R and antibodies thereto, such as the antibodies of the invention or screening of peptide libraries, therapeutic peptides can be generated that are directed against IL-6Rc and/or both IL-6Rc and IL-6R. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the IL-6Rc and/or both IL-6Rc and IL-6R molecule (or a form, such as a splice variant or alternate form) is functionally active in a disease process, it will also be possible to design gene and antisense therapeutics thereto through conventional techniques. Such modalities can be utilized for modulating the function of IL-6Rc. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the IL-6Rc molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of IL-6Rc. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of IL-6Rc to gp130, or candidate or test compounds or agents that modulate or otherwise interfere with the signaling function of the IL-6 receptor. Also provided are methods of identifying compounds useful to treat disorders associated with aberrant IL-6 signaling. The invention also includes compounds identified in the screening assays described herein.

In one embodiment, the invention provides assays for screening candidate or test compounds which modulate the signaling function of IL-6Rc. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates the signaling function of IL-6Rc and/or the interaction between IL-6 and IL-6R. For example, the antibody is monoclonal antibody 39B9 VL1 and the antigen is IL-6R. Alternatively, the monoclonal antibody is 39B9 VL5, 12A, or 5C, and the antigen is IL-6Rc or IL-6R.

In another embodiment, a soluble IL-6Rc and/or both IL-6Rc and IL-6R protein of the invention is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant IL-6 signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a neutralizing antibody, such as monoclonal antibody 39B9 VL1, 39B9 VL5, 12A and 5C, each of which modulates or otherwise interferes with IL-6 mediated activation of the JAK/STAT pathway and/or MAPK cascade.

The screening methods disclosed herein may be performed as a cell-based assay or as a cell-free assay. The cell-free assays of the invention are amenable to use of either the soluble form or the membrane-bound form of IL-6Rc and/or both IL-6Rc and IL-6R, and fragments thereof. In the case of cell-free assays comprising the membrane-bound forms of IL-6Rc and/or both IL-6Rc and IL-6R it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. 39B9 VL1, 39B9 VL5, 12A and 5C) or the antigen (e.g. IL-6Rc and/or both IL-6Rc and IL-6R protein) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic and Prophylactic Formulations

The huIL-6Rc MAbs of the invention are used in diagnostic and prophylactic formulations. In one embodiment, an IL-6Rc and/or both IL-6Rc and IL-6R antagonist, such as a huIL-6Rc MAb of the invention, is administered to patients that are at risk of developing one or more of the aforementioned diseases, such as for example, without limitation, sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus). A patient's or organ's predisposition to one or more of the aforementioned autoimmune or inflammatory diseases can be determined using genotypic, serological or biochemical markers.

In another embodiment of the invention, an IL-6Rc and/or both IL-6Rc and IL-6R antagonist, such as a huIL-6Rc antibody is administered to human individuals diagnosed with a clinical indication associated with one or more of the aforementioned diseases, such as for example, without limitation, sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus). Upon diagnosis, an IL-6Rc and/or both IL-6Rc and IL-6R antagonist, such as a huIL-6Rc antibody is administered to mitigate or reverse the effects of the clinical indication associated with one or more of the aforementioned diseases, such as for example, without limitation, sepsis, cancer (e.g., multiple myeloma disease (MM), renal cell carcinoma (RCC), plasma cell leukaemia, lymphoma, B-lymphoproliferative disorder (BLPD), and prostate cancer), bone resorption, osteoporosis, cachexia, psoriasis, mesangial proliferative glomerulonephritis, Kaposi's sarcoma, AIDS-related lymphoma, and inflammatory diseases (e.g., rheumatoid arthritis, systemic onset juvenile idiopathic arthritis, hypergammaglobulinemia, Crohn's disease, ulcerative colitis, systemic lupus erythematosus (SLE), multiple sclerosis, Castleman's disease, IgM gammopathy, cardiac myxoma, asthma, allergic asthma and autoimmune insulin-dependent diabetes mellitus).

Antibodies of the invention are also useful in the detection of IL-6Rc and/or both IL-6Rc and IL-6R in patient samples and accordingly are useful as diagnostics. For example, the huIL-6Rc antibodies of the invention are used in in vitro assays, e.g., ELISA, to detect IL-6Rc and/or both IL-6Rc and IL-6R levels in a patient sample.

In one embodiment, a huIL-6Rc antibody of the invention is immobilized on a solid support (e.g., the well(s) of a microtiter plate). The immobilized antibody serves as a capture antibody for any IL-6Rc and/or both IL-6Rc and IL-6R that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of IL-6Rc and/or both IL-6Rc and IL-6R antigen in the test sample is determined by comparison with a standard curve developed from the standard samples.

It will be appreciated that based on the results obtained using the huIL-6Rc antibodies of the invention in an in vitro diagnostic assay, it is possible to stage a disease (e.g., a clinical indication associated with ischemia, an autoimmune or inflammatory disorder) in a subject based on expression levels of the IL-6Rc and/or both IL-6Rc and IL-6R antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Cloning, Expression and Purification of Interleukin-6 (IL-6), IL-6 Receptor (IL-6R) and the Complex of IL-6/IL-6R (IL-6Rc)

The cDNAs encoding the human IL-6R (Accession No. X12830), human IL-6 (Accession No. BC015511), cynomolgus IL-6R, cynomolgus IL-6 (Accession No. AB000554), mouse IL-6R (Accession No. NM_010559) and mouse IL-6

(Accession No. NM_031168) were amplified by PCR from peripheral blood mononuclear cells (PMBC)-derived cDNA and cloned in PCR4TOPO vector (Invitrogen). Following a subsequent PCR step, a His- or Avi-Tag (Avidity, Denver Colo.) was introduced at the C-terminus of the cytokine coding sequence. These constructs were then sub-cloned into corresponding vectors for expression of either the soluble or membrane forms of IL-6, IL-6R and IL-6Rc. The soluble human IL-6Rc (shuIL-6Rc) recombinant protein was generated by fusing IL-6 to IL-6R (the fusion protein of IL-6/IL-6R taken from Mizuguchi et al., 2001 *J. Biosci. Bioeng.* 91(3): 299-304 with modifications as follows: aa1-333 for IL-6R and aa28-212 for IL-6). His-tagged coding sequences of cytokines from various species (human, cynomolgus, mouse) were placed under the control of the EF1 promoter and/or CMV promoter for expression in the episomal expression vector pEAK8 or pEE14.4 for soluble forms. The cytokine-coding sequence was followed by a viral internal ribosome entry site (IRES) and a second or third cistron for the co-expression of BirA and GFP. The pEAK8 vector contains the puromycin resistance gene, the EBV nuclear antigen 1 (EBNA1) and the oriP origin of replication. EBNA1 and oriP are necessary for the propagation of the pEAK8 vector as episomal DNA in human cells and the generation of stable transfectants. Stably transfected cells were obtained after 7-10 days of culture in the presence of 2 ug/mL of puromycin. Puromycin-resistant cells were expanded and used for soluble cytokine production. The biological activity of the soluble His-tagged, human, mouse and cynomolgus, IL-6R, IL-6 and IL-6Rc was tested in various functional assays and found to be comparable to reagents from commercial sources (where available). For cell surface expression the IL-6R, IL-6 and IL-6Rc constructs were cloned into the pDisplay vector, transected into CHO cells and selected with G418 selection.

Example 2

Immunizations

Fully human monoclonal antibodies were generated using transgenic strains of mice in which mouse antibody gene expression was suppressed and replaced with human antibody gene expression. Three strains of transgenic mice were used:
1) HuMab® mouse (Medarex, Princeton N.J.)
2) KM™ mouse, a crossbred between HuMAb Mouse and Kirin's TC Mouse (Kirin Pharma Company, Japan)
3) KM (FCγRIIb-KO) mouse, a strain derived from KM™ mouse, in which the gene Fcgr2b coding for the inhibitory Fc gamma Receptor IIB has been inactivated.

Mice were immunized either with Chinese Hamster Ovary expressing human IL-6Rc at the cell surface (CHO/IL-6Rc) or with soluble human IL-6Rc (shuIL-6Rc).

In general, all animals received from 7 to 10 injections intraperitoneally (i.p.) or subcutaneously (s.c.) with CHO/IL-6Rc or IL-6Rc emulsified in MPL+TDM adjuvant (RIBI) as described herein. The initial 5 to 8 injections were all done in the presence of adjuvant. The two final hyperboosts preceding the fusion were done with free antigen and without adjuvant. An example of a representative immunization schedule:

| Day 1  | $10^7$ CHO/IL-6Rc cells, i.p. in RIBI |
| Day 14 | $10^7$ CHO/IL-6Rc cells, i.p. in RIBI |
| Day 28 | $10^7$ CHO/IL-6Rc cells, i.p. in RIBI |
| Day 42 | 50μg shuIL-6Rc, i.p. in RIBI |

-continued

| Day 56 | 20μg shuIL-6Rc, s.c. in RIBI |
| Day 70 | 10μg shuIL-6Rc, s.c. in PBS |
| Day 84 | 10μg shuIL-6Rc, s.c. in PBS |
| Day 87 | 5μg shuIL-6Rc, s.c. in PBS |

Sera of immunized animals were screened periodically by flow cytometric analysis to detect the presence of human IgG directed to CHO/IL-6Rc as compared to CHO cells alone. To obtain hybridomas, popliteal, inguinal, para-aortic, submandibular, cervical, axial, and brachial lymph nodes were removed from the mice and digested with collagenase and DNAse. Single cells suspension of lymph node cells was mixed at 1:1 ratio with SP2/0 myeloma cells and suspended in Cytofusion Low Conductivity Medium (CPS-LCMC, CytoPulse Sciences, Inc.). Fusions were done with 30 to 60 million splenocytes in the CytoPulse CEEF50 Electrofusion apparatus as indicated by the manufacturer (Cyto Pulse Sciences, Inc). After electrofusion, cells were incubated for approximately 1 hour at 37° C. to allow recovery before distributing into 96-well plates. Fused cells were resuspended in HAT selection medium and plated in 44 to 52 96-well plates at a cell concentration of $0.1$-$0.2 \times 10^5$ splenocytes per well in 200 μl medium. Hybridoma selection proceeded for 14 days. Fusion of lymph nodes of immunized mice resulted in the generation of hybridomas producing antibodies specific to IL-6Rc. Fourteen days after the fusion, hybridoma-containing plates were screened for the presence of human IgG binding to human CHO/IL-6Rc.

Example 3

Biological Assays for IL-6Rc Activity

All assays described herein were performed in parallel with a control human IgG1 monoclonal antibody to human IL-6R (U.S. Pat. No. 5,817,790, SEQ ID NO:69 and SEQ ID NO: 71); hereto referred as "control mAb". Furthermore, the 39B9 VL1 antibody (nucleic acid sequences SEQ ID NO: 1 and 3, amino acid sequences SEQ ID NO: 2 and 4) has been designated the nomenclature "NI-1201".

On target cells, IL-6 first binds to the membrane-bound IL-6R (mIL-6R). The complex of IL-6/IL-6R associates with the signal-transducing membrane protein gp130, thereby promoting its dimerization and the subsequent initiation of intracellular signaling. gp130 is ubiquitously expressed by cells whereas mIL-6R has a reduced expression profile on hepatocytes and a restricted number of immune cells. A naturally occurring, soluble form of the IL-6R (sIL6R) is generated by proteolysis of the membrane form or by differential splicing of IL-6R mRNA. The sIL-6R combines with IL-6 to form the soluble IL-6/IL-6R complex (IL-6Rc) and is capable of activating mIL-6R-negative gp130-positive cells. This mechanism is called trans-signaling whereas signaling via IL-6 binding to mIL-6R and subsequent coupling to gp130 is termed cis-signaling (Taga et al., 1989, Cell, 58: 573-581).

Figure 2:
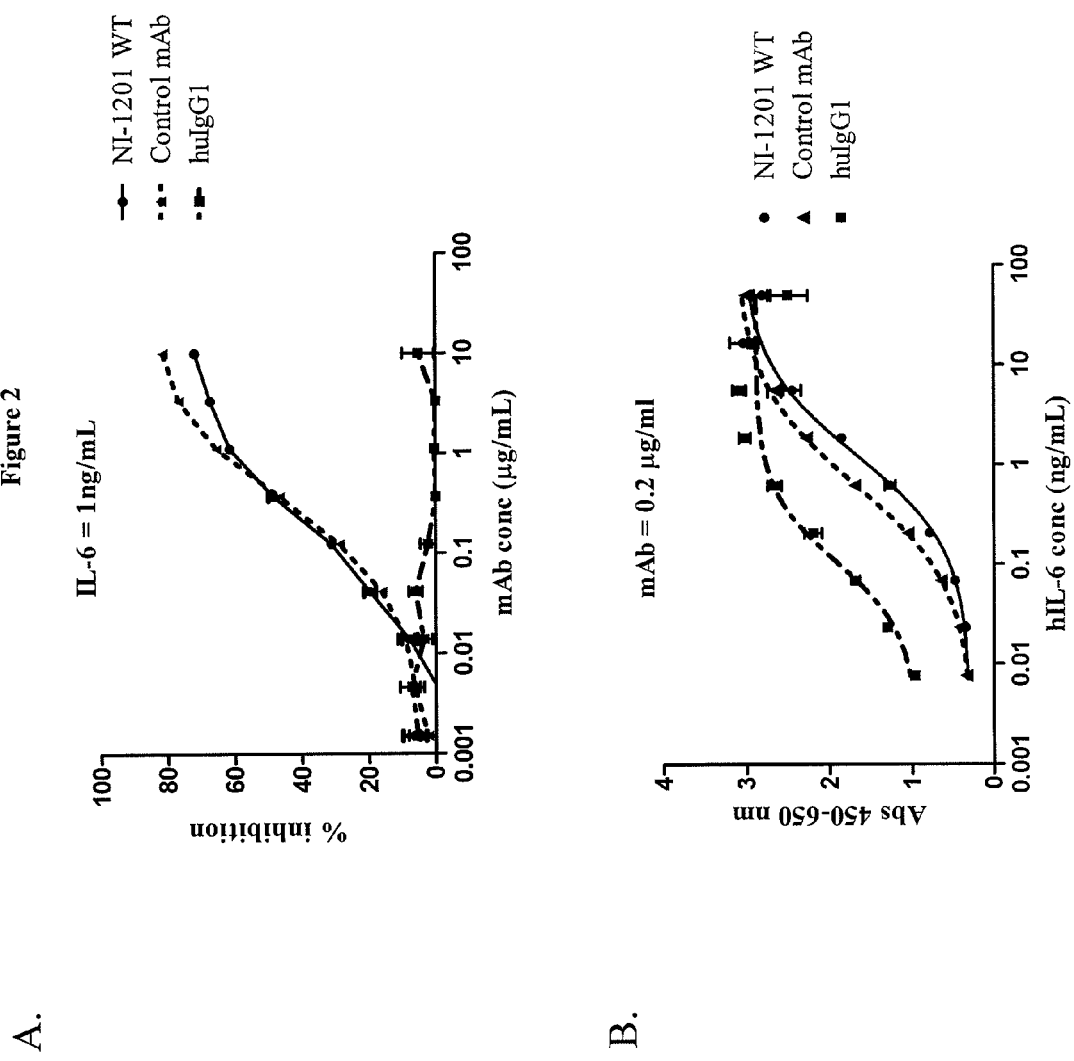
FIGS. 2A and 2B are a series of graphs depicting the ability of the NI-1201 antibody to block IL-6 cis-signaling.

IL-6 functional assays: BAF-hugp130 cells (BAF-130), a human gp130-transfected mouse pro-B cell line, proliferate in the presence of IL-6 and shuIL-6R (FIG. 1). Similarly, BAF-130 cells transfected with membrane bound huIL-6R (BAF-130/IL-6R) proliferate when cultured with huIL-6 (FIG. 2).

For trans-signaling analysis, the "native" IL-6Rc (as opposed to recombinant the fusion complex) was formed by incubating the cytokine (IL-6) with its cognate soluble receptor (shuIL-6R) at 37° C. for 3-4 h. Several concentrations of mAbs were added on cells before culturing with the native complex. BAF-130 cells (1×10⁴ cells/0.2 mL/well) were incubated for 72 h in a 96-well flat-bottom plate in RPMI supplemented with 0.5% fetal calf serum in the presence of test mAbs (Control mAb, huIgG1 or NI-1201) with huIL-6+ shuIL-6R (FIG. 1A-D). Proliferation was assessed using the cell proliferation reagent WST-1 (Roche) according to manufacturer's instructions. Briefly, after the culture period, 20 μL of WST-1 reagent were added in medium and incubated at 37° C. 5% CO2 for 4 hours. Absorbance (450-650 nm) was measured using a microplate reader. Results demonstrate that NI-1201 neutralizes the activity of the native IL-6Rc more effectively than the control mAb.

For cis-signaling analysis, BAF-130/IL-6R cells were incubated with different doses of mAbs and a fixed amount of IL-6 (FIG. 2A). Conversely, cells were also incubated with one concentration of mAb in the presence of ascending amounts of IL-6 (FIG. 2B). Proliferation was assessed using the cell proliferation reagent WST-1 as above. NI-1201 and control mAb demonstrate equivalent activity in blocking this cis-signaling assay.

Example 4

Variants of huIL-6Rc Antibodies

Variants of the huIL-6Rc antibodies are made using any of a variety of art-recognized techniques. For example, variant huIL-6Rc antibodies include antibodies having one or more amino acid modifications, such as, for example, an amino acid substitution, at position within the antibody sequence.

Preferred locations for amino acid substitutions are shown as bold, underlined residues below in Table 3. The amino acid residues in bold/underline can be replaced with any amino acid residue. In preferred embodiments, the amino acid residues in bold/underline are replaced with the amino acid residues shown below in Table 3. In these embodiments, the antibody comprises (i) the consensus amino acid sequence QQSXSYPLT (SEQ ID NO: 42) in the light chain complementarity determining region 3 (CDR3), where X is N or Q; (ii) the consensus amino acid sequence GIIPX$_1$FX$_2$TTKYAQX$_3$FQG (SEQ ID NO: 43) in the heavy chain complementarity determining region 2 (CDR2), where X$_1$ is L or A, X$_2$ is D or E, and X$_3$ is Q or K; (iii) the consensus amino acid sequence DRDILTDYYPXGGMDV (SEQ ID NO: 44) in the heavy chain complementarity determining region 3 (CDR3), where X is M or L; and (iv) the consensus amino acid sequence TAVXYCAR (SEQ ID NO: 45) in the framework region 3 (FRW3), where X is F or Y.

The NI-1201-wild type (NI-1201-WT) antibody listed in Table 3 comprises the amino acid sequence QQSNSYPLT (SEQ ID NO: 26) in the light chain CDR3 region, the amino acid sequence GIIPLFDTTKYAQQFQG (SEQ ID NO: 16) in the heavy chain CDR2 region, the amino acid sequence DRDILTDYYPMGGMDV (SEQ ID NO: 36) in the heavy chain CDR3 region, and the amino acid sequence TAVFYCAR (SEQ ID NO: 38) in the FRW3 region.

The NI-1201-A antibody listed in Table 3 comprises the amino acid sequence QQSNSYPLT (SEQ ID NO: 26) in the light chain CDR3 region, the amino acid sequence GIIPLFDTTKYAQKFQG (SEQ ID NO: 33) in the heavy chain CDR2 region, the amino acid sequence DRDILTDYYPMGGMDV (SEQ ID NO: 36) in the heavy chain CDR3 region, and the amino acid sequence TAVYYCAR (SEQ ID NO: 39) in the FRW3 region.

The NI-1201-B antibody listed in Table 3 comprises the amino acid sequence QQSNSYPLT (SEQ ID NO: 26) in the light chain CDR3 region, the amino acid sequence GIIPLFDTTKYAQKFQG (SEQ ID NO: 33) in the heavy chain CDR2 region, the amino acid sequence DRDILTDYYPLGGMDV (SEQ ID NO: 37) in the heavy chain CDR3 region, and the amino acid sequence TAVYYCAR (SEQ ID NO: 39) in the FRW3 region.

The NI-1201-C antibody listed in Table 3 comprises the amino acid sequence QQSNSYPLT (SEQ ID NO: 26) in the light chain CDR3 region, the amino acid sequence GIIPAFETTKYAQKFQG (SEQ ID NO: 34) in the heavy chain CDR2 region, the amino acid sequence DRDILTDYYPLGGMDV (SEQ ID NO: 37) in the heavy chain CDR3 region, and the amino acid sequence TAVYYCAR (SEQ ID NO: 39) in the FRW3 region.

The NI-1201-D antibody listed in Table 3 comprises the amino acid sequence QQSQSYPLT (SEQ ID NO: 32) in the light chain CDR3 region, the amino acid sequence GIIPAFETTKYAQKFQG (SEQ ID NO: 34) in the heavy chain CDR2 region, the amino acid sequence DRDILTDYYPLGGMDV (SEQ ID NO: 37) in the heavy chain CDR3 region, and the amino acid sequence TAVYYCAR (SEQ ID NO: 39) in the FRW3 region.

The NI-1201-E antibody listed in Table 3 comprises the amino acid sequence QQSQSYPLT (SEQ ID NO: 32) in the light chain CDR3 region, the amino acid sequence GIIPLFDTTKYAQKFQG (SEQ ID NO: 33) in the heavy chain CDR2 region, the amino acid sequence DRDILTDYYPLGGMDV (SEQ ID NO: 37) in the heavy chain CDR3 region, and the amino acid sequence TAVYYCAR (SEQ ID NO: 39) in the FRW3 region.

The NI-1201-F antibody listed in Table 3 comprises the amino acid sequence QQSNSYPLT (SEQ ID NO: 26) in the light chain CDR3 region, the amino acid sequence GIIPAFDTTKYAQKFQG (SEQ ID NO: 35) in the heavy chain CDR2 region, the amino acid sequence DRDILTDYYPLGGMDV (SEQ ID NO: 37) in the heavy chain CDR3 region, and the amino acid sequence TAVYYCAR (SEQ ID NO: 39) in the FRW3 region.

The NI-1201-G antibody listed in Table 3 comprises the amino acid sequence QQSQSYPLT (SEQ ID NO: 32) in the light chain CDR3 region, the amino acid sequence GIIPAFDTTKYAQKFQG (SEQ ID NO: 35) in the heavy chain CDR2 region, the amino acid sequence DRDILTDYYPLGGMDV (SEQ ID NO: 37) in the heavy chain CDR3 region, and the amino acid sequence TAVYYCAR (SEQ ID NO: 39) in the FRW3 region.

TABLE 3

NI-1201 Lead Candidates

| | Light chain CDR3 | Heavy chain CDR2 | Heavy chain CDR3 | FRW 3 |
| --- | --- | --- | --- | --- |
| NI1201-WT | QQSNSYPLT | GIIPLFDTTKYAQQFQG | DRDILTDYYPMGGMDV... | TAVFYCAR... |
| NI1201-A | QQSNSYPLT | GIIPLFDTTKYAQKFQG | DRDILTDYYPMGGMDV | ...TAVYYCAR... |

TABLE 3-continued

NI-1201 Lead Candidates

|  | Light chain CDR3 | Heavy chain CDR2 | Heavy chain CDR3 | FRW 3 |
|---|---|---|---|---|
| NI1201-B | QQSNSYPLT | GIIPLFDTTKYAQKFQG | DRDILTDYYPLGGMDV | ...TAVYYCAR... |
| NI1201-C | QQSNSYPLT | GIIPAFETTKYAQKFQG | DRDILTDYYPLGGMDV | ...TAVYYCAR... |
| NI1201-D | QQSQSYPLT | GIIPAFETTKYAQKFQG | DRDILTDYYPLGGMDV | ...TAVYYCAR... |
| NI1201-E | QQSQSYPLT | GIIPLFDTTKYAQKFQG | DRDILTDYYPLGGMDV | ...TAVYYCAR... |
| NI1201-F | QQSNSYPLT | GIIPAFDTTKYAQKFQG | DRDILTDYYPLGGMDV | ...TAVYYCAR... |
| NI1201-G | QQSQSYPLT | GIIPAFDTTKYAQKFQG | DRDILTDYYPLGGMDV | ...TAVYYCAR... |

Example 5

NI-1201 Blocks STAT-3 Phosphorylation Induced by IL-6 Cis-Signaling

Figure 3:
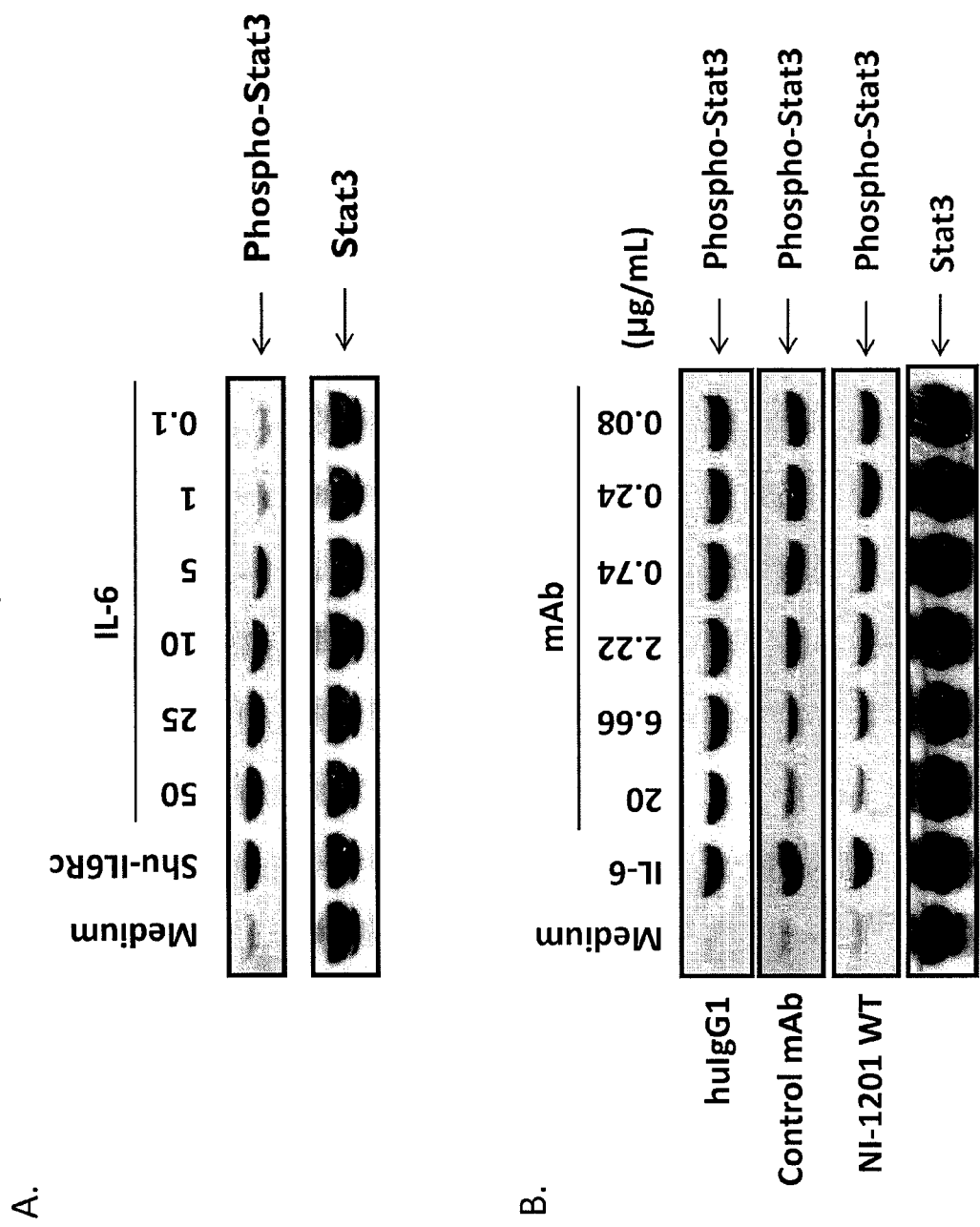
FIGS. 3A and 3B are a series of illustrations depicting the ability of the NI-1201 antibody to block STAT-3 phosphorylation induced by IL-6 cis-signaling.

After a 24 h serum starvation, the mIL-6R-positive human hepatocellular carcinoma HepG2 cells (ATCC) were incubated for 10 min with indicated concentrations of hIL-6 (FIG. 3A) or with 10 ng/mL IL-6 with indicated concentrations of huIgG1, control mAb or NI-1201 WT (FIG. 3B). After lysis in sample buffer, proteins were analyzed in SDS-PAGE western blotting using a monoclonal anti-phospho-STAT3 antibody, P-STAT3 (Cell signaling technology). The blots were stripped and re-probed with a polyclonal antibody recognizing activated and non activated STAT3 (Santa Cruz Biotechnology). NI-1201 and control mAb demonstrated equivalent activity in blocking the cis-signaling induced phosphorylation of STAT-3.

Example 6

NI-1201 Blocks IL-6 Trans-Signaling Mediated by shuIL-6Rc

Figure 4:
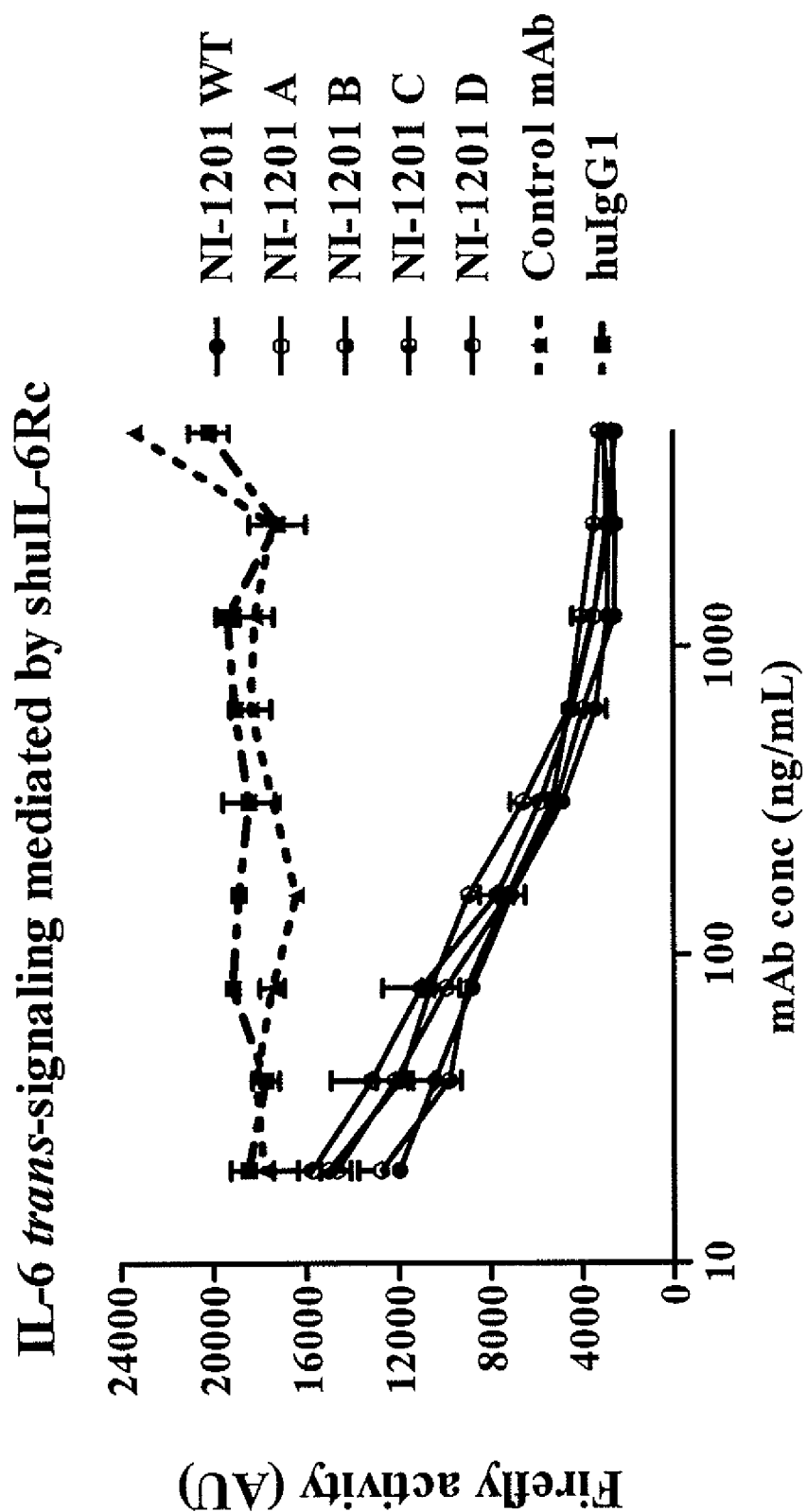
FIG. 4 is a graph depicting the ability of the NI-1201 antibody to block IL-6 trans-signaling mediated by the fusion protein of soluble human IL-6/IL-6R complex ("shuIL-6Rc").

PEAK cells were transiently transfected with the Luciferase reporter plasmid (promoter STAT3 dependent). $2.5 \times 10^4$ cells per well were seeded into 96-well flat-bottomed plates in DMEM containing 0.5% fetal calf serum. After 4-6 h cell adhesion, PEAK cells were activated with 30 ng/mL of shuIL-6Rc with ascending doses of indicated mAbs. 18 h later, medium was removed and the Luciferase assay was carried out using the steady-Glo® Luciferase Assay system (Promega) in a chemoluminescence analyzer. All variants of NI-1201 neutralized, in a dose dependant fashion, the activity of shuIL-6Rc whereas the control mAb failed to block the activity of the pre-formed complex (FIG. 4).

Example 7

Affinity and Binding Kinetics of huIL-6Rc Antibodies

Figure 5:
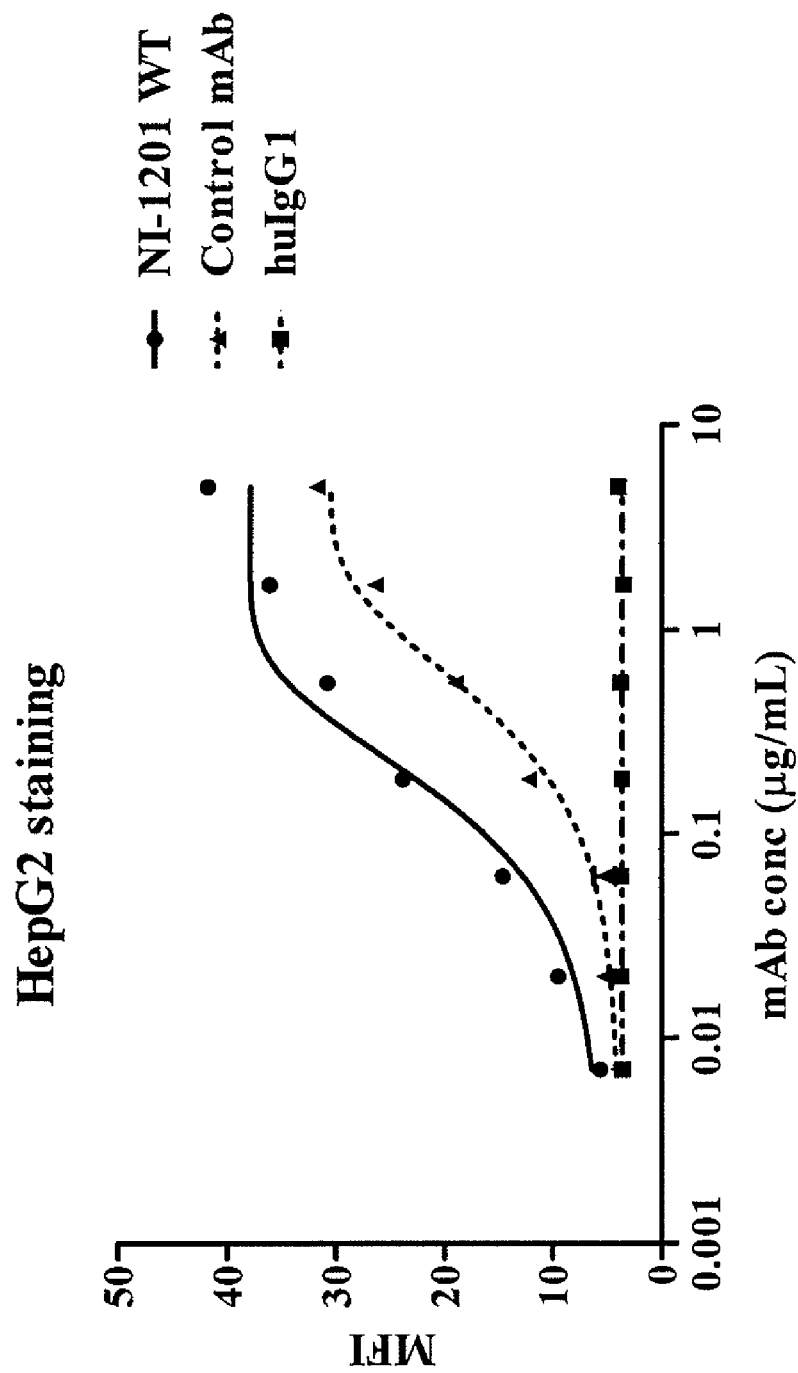
FIG. 5 is a graph depicting the binding of the NI-1201 antibody to membrane-bound IL-6R.

The ability of NI-1201 to bind to native membrane bound huIL-6R was evaluated using flow cytometric analysis on the HepG2 hepatoma cell line. Cell surface staining is performed on HepG2 cells with different doses of mAbs. Binding of primary unconjugated mAbs (Control mAb, huIgG1 and NI-1201 mAbs) was detected with goat anti-human Alexa Fluor 647 IgG (H+L) (Invitrogen). Each experiment was performed in triplicates. The mean of fluorescence intensity (MFI) is represented and demonstrates an apparent increased affinity of NI-1201 for the membrane IL-6R as compared to the control mAb (FIG. 5).

The affinity and binding kinetics of NI-1201 candidates (A-D), NI-1201 WT and control mAb were characterized on a Biacore 2000 instrument (Biacore AB, Uppsala, Sweden). A CM5 Biacore chip was used and 1640 RU (response units) of an anti-human IgG Fc (Biacore AB, Uppsala, Sweden) was immobilized by EDC/NHS chemistry. This surface was used to capture NI-1201 candidates, NI-1201 WT and the control mAb. The surface was regenerated after each cycle by injection of 3M magnesium chloride at 20 µL/min, for 30 s followed by 1 min of stabilization time in HBS-EP buffer (Biacore AB, Uppsala, Sweden). Binding was measured by passing analytes carrier-free soluble human IL-6R (shuIL-6R; R&D), soluble human IL-6Rc (shuIL-6Rc) and soluble cynomolgus monkey IL-6R (scyIL-6R) in duplicates at the following concentrations: 100 nM, 50 nM, 25 nM, 12.5 nM, 6.25 nM and 0 nM. All solutions were diluted in HBS-EP buffer. Injection was performed at 50 µl/min for 3 min followed by 12 min of dissociation time and the temperature was set at 25° C. The data were fitted according to 1:1 Langmuir model and the $K_{on}$, $K_{off}$ and $K_D$ values determined. The affinities and kinetic constants of NI-1201 variants A-D, NI-1201 WT and control mAb are summarized in the Table 4. Confirming the functional assays using either native or preformed IL-6Rc, NI-1201 demonstrated a sub-nanomolar affinity for the complex whereas the control mAb exhibited no measurable binding.

TABLE 2

Kinetic and affinity constants measured by Biacore

| Analyte | Sample | $K_{on}$ (1/Ms) | $K_{off}$ (1/s) | $K_D$ (M) |
|---|---|---|---|---|
| shuIL-6R | NI-1201 A | 8.29E + 05 | 1.10E-04 | 1.21E-10 |
|  | NI-1201 B | 8.75E + 05 | 9.40E-05 | 1.07E-10 |
|  | NI-1201 C | 9.92E + 05 | 1.10E-04 | 1.10E-10 |
|  | NI-1201 D | 7.61E + 05 | 1.02E-04 | 1.34E-10 |
|  | NI-1201 WT | 1.33E + 06 | 7.53E-05 | 5.67E-11 |
|  | Control mAb | 4.14E + 05 | 3.99E-04 | 9.65E-10 |
| shuIL-6Rc | NI-1201 A | 5.01E + 04 | 2.46E-04 | 4.92E-09 |
|  | NI-1201 B | 5.34E + 04 | 2.37E-04 | 4.43E-09 |
|  | NI-1201 C | 4.77E + 04 | 2.40E-04 | 5.03E-09 |
|  | NI-1201 D | 4.53E + 04 | 2.22E-04 | 4.89E-09 |
|  | NI-1201 WT | 4.31E + 04 | 2.43E-04 | 5.64E-09 |
|  | Control mAb | N.D. | N.D. | N.D. |
| scyIL-6R | NI-1201 A | 1.04E + 05 | 2.13E-04 | 2.05E-09 |
|  | NI-1201 B | 1.15E + 05 | 2.07E-04 | 1.81E-09 |
|  | NI-1201 C | 1.11E + 05 | 2.25E-04 | 2.03E-09 |
|  | NI-1201 D | 1.12E + 05 | 2.00E-04 | 1.79E-09 |
|  | NI-1201 WT | 1.06E + 05 | 2.15E-04 | 2.04E-09 |
|  | Control mAb | 2.68E + 04 | 4.63E-04 | 1.73E-08 | shuIL-6R = soluble human IL-6 Receptor;
shuIL-6Rc = soluble human IL-6/IL-6 Receptor complex;
scyIL-6R = soluble cynomolgus monkey IL-6 Receptor;
N.D. = no binding detected.

Example 8

Epitope Mapping of huIL-6Rc Antibodies

Construction of IL-6R chimeras and mutated mouse IL-6R: Each modification was performed on the soluble form of IL-6R and added in a pDISPLAY™ vector (Invitrogen) allowing surface expression of constructs. Epitope mapping of NI-1201 was assessed by exchanging human residues in the second fibronectin II domain (D3 domain) of mouse IL-6R and by verifying if binding of mAbs on modified mouse IL-6R was recovered.

Figure 6:
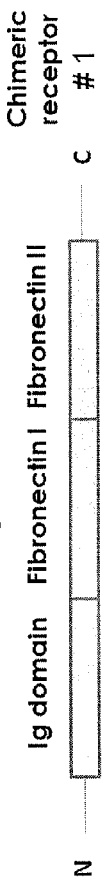
FIGS. 6A-6D are a series of illustrations and graphs depicting the mapping of the NI-1201 epitope on IL-6R.
Figure 6:
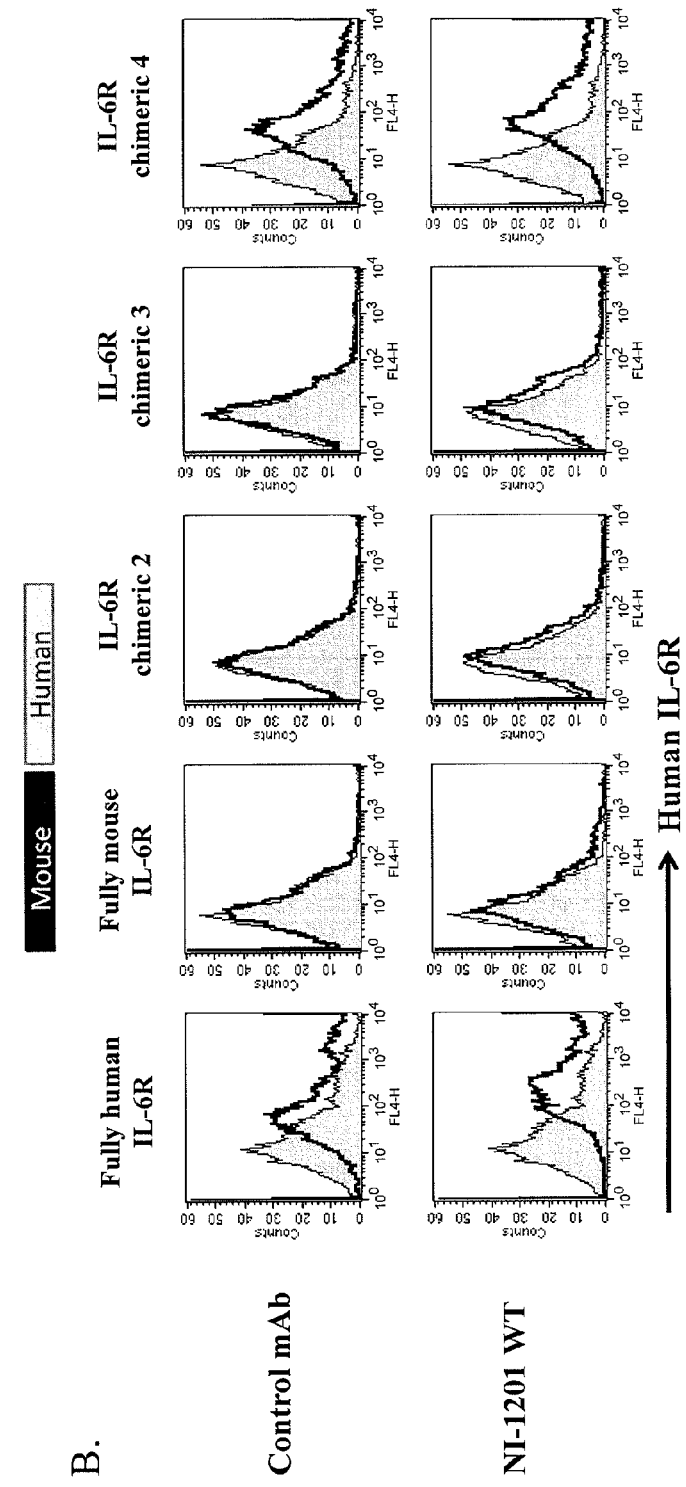

An overlap extension PCR strategy was used to generate coding sequences specifying huIL-6R/mouseIL-6R chimeric proteins (FIG. 6A) and mouse IL-6R proteins containing human amino acid substitutions in D3 domains (FIG. 6B). Partially overlapping mutagenic oligonucleotide primers were used for PCR amplification of N- and C-terminal sequences on either side of huIL-6R/mouse IL-6R junctions or substituted regions, followed by gel isolation and annealing of the denatured PCR products. Full length PCR products were then digested by EcoRI and BglII and ligated into a pDISPLAY™ vector (Invitrogen). PEAK cells were grown in DMEM medium supplemented with 10% fetal calf serum and 4 mM L-glutamine. Cells were plated 12 to 24 h before transfection to have 40-50% confluency in 6 well plates. Transfections of pDISPLAY™ vectors (Invitrogen) were carried out by lipofection using TransIT® LT1 reagent (Mirus-Bio) according manufacturer's specifications. Cells were grown for 48 h before harvesting and analysis by flow cytometry.

FACS analysis: Cell surface staining was performed on PEAK cells displaying each variant of IL-6R and analyzed by flow cytometry (FIG. 6B-D). Cell surface expression of each chimeric IL-6R was assessed using an anti human-CD126 PE or an anti-mouse CD126-PE antibody (BD Pharmingen). Control mAb and NI-1201 binding was detected using a goat anti-human IgG (H+L) Alexa Fluor 647 (Invitrogen). Data demonstrated that NI-1201 recognizes a distinct epitope on huIL-6R to the Control mAb.

Example 9

NI-1201 Cross-Reacts and Neutralizes Cynomolgus Monkey IL-6Rc

Figure 7:
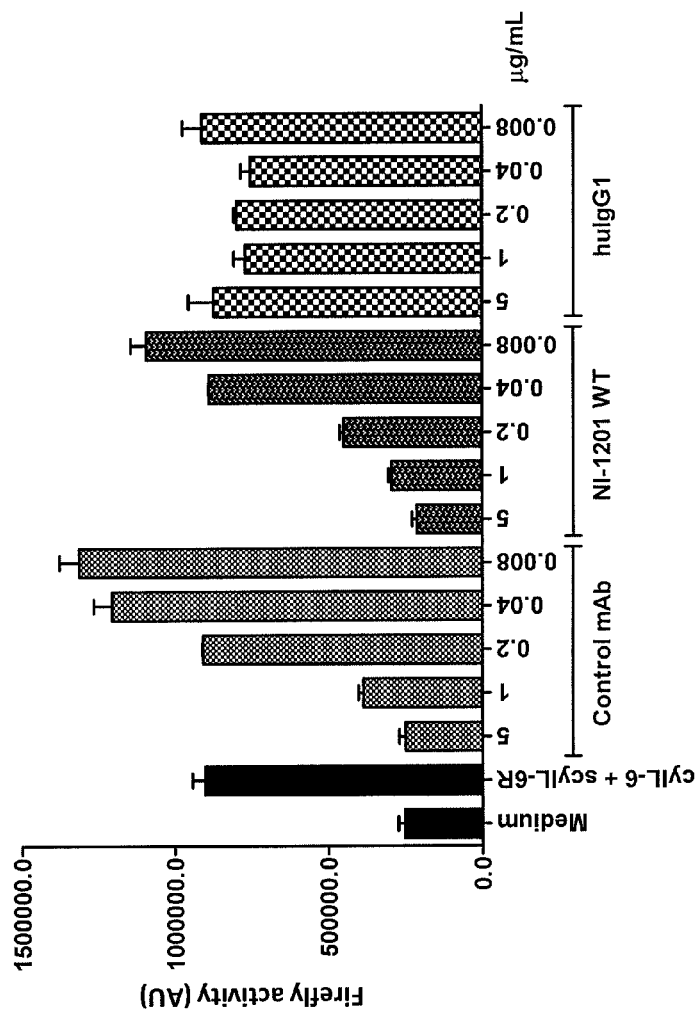
FIGS. 7A and 7B are an illustration and a graph depicting the ability of the NI-1201 antibody to cross-react and neutralize cynomolgus monkey IL-6 signaling.

IL-6R protein sequence homology between human and indicated species is shown (FIG. 7A). As described in example 6, PEAK cells were transiently transfected with the Luciferase reporter plasmid (STAT3-dependent promoter) and activated with 25 ng/mL cynomolgus IL-6+250 ng/mL scyIL-6R with different doses of indicated anti-human mAbs. Luciferase assay was carried out as described above in Example 6 (FIG. 7B). Results demonstrated the capacity of NI-1201 to neutralize the functional activity of native cynomolgus IL-6Rc.

What is claimed is:

1. An isolated fully human monoclonal anti-IL-6/IL-6R complex (IL-6Rc) antibody, or antigen-binding fragment thereof, wherein said antibody comprises:

(a) a $V_H$ CDR1 region comprising the amino acid sequence of SEQ ID NO: 15;

(b) a $V_H$ CDR2 region comprising the amino acid sequence of SEQ ID NO: 33;

(c) a $V_H$ CDR3 region comprising the amino acid sequence of SEQ ID NO: 36;

(d) a $V_L$ CDR1 region comprising the amino acid sequence of SEQ ID NO: 24;

(e) a $V_L$ CDR2 region comprising the amino acid sequence of SEQ ID NO: 25; and (f) a $V_L$ CDR3 region comprising the amino acid sequence of SEQ ID NO: 26, wherein said antibody binds the IL-6/IL-6R complex.

2. The antibody of claim 1, wherein said antibody also binds the IL-6R.

3. The antibody of claim 1, wherein said antibody is an IgG isotype.

4. The antibody of claim 1, wherein said antibody is an IgG1 isotype.

5. The antibody of claim 1, wherein said antibody comprises the amino acid sequence of SEQ ID NO: 39 in the framework 3 (FRW3) region of the variable heavy chain.

6. A pharmaceutical composition comprising the antibody of claim 1 and a carrier.

* * * * *

SEQUENCE LISTING

```
<160> NUMBER OF SEQ ID NOS: 46

<210> SEQ ID NO 1
<211> LENGTH: 375
<212> TYPE: DNA
<213> ORGANISM: Homo sapiens

<400> SEQUENCE: 1
caggtgcagc tggtgcagtc tggggctgag gtgaagaagc ctgggtcctc ggtgaaggtc      60
tcctgcaagg cttctggagg caccttcagc agctatgcta tcagctgggt gcgccaggcc     120
cctggacaag ggcttgagtg gatgggaggg atcatccctc tctttgatac aacaaagtac     180
gcacagcagt tccagggcag agtcacgatt accgcggacg aatccacgag cacagcctac     240
atggagctga gcagcctgag atctgaggac acggccgtat tttactgtgc gagagatcgg     300
gatattttga ctgattatta tcccatgggc ggtatggacg tctggggcca agggaccacg     360
gtcaccgtct cctca                                                      375

<210> SEQ ID NO 2
<211> LENGTH: 125
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Ile Pro Leu Phe Asp Thr Thr Lys Tyr Ala Gln Gln Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Phe Tyr Cys
                 85                  90                  95
Ala Arg Asp Arg Asp Ile Leu Thr Asp Tyr Tyr Pro Met Gly Gly Met
                100                 105                 110
Asp Val Trp Gly Gln Gly Thr Thr Val Thr Val Ser Ser
            115                 120                 125

<210> SEQ ID NO 3
<211> LENGTH: 324
<212> TYPE: DNA
<213> ORGANISM: Homo sapiens

<400> SEQUENCE: 3
gccatccagt tgacccagtc tccatcctcc ctgtctgcat ctgtaggaga cagagtcacc      60
atcacttgcc gggcaagtca gggcattagc agtgttttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tctaatagtt acccgctcac tttcggcgga     300
gggaccaagg tggagatcaa acgt                                            324

<210> SEQ ID NO 4
<211> LENGTH: 108
<212> TYPE: PRT
<213> ORGANISM: Homo sapiens

<400> SEQUENCE: 4

Ala Ile Gln Leu Thr Gln Ser Pro Ser Ser Leu Ser Ala Ser Val Gly
 1               5                  10                  15
Asp Arg Val Thr Ile Thr Cys Arg Ala Ser Gln Gly Ile Ser Ser Val
                 20                  25                  30
Leu Ala Trp Tyr Gln Gln Lys Pro Gly Lys Ala Pro Lys Leu Leu Ile
             35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Asn Ser Tyr Pro Leu
                 85                  90                  95
Thr Phe Gly Gly Gly Thr Lys Val Glu Ile Lys Arg
                100                 105

<210> SEQ ID NO 5
<211> LENGTH: 324
<212> TYPE: DNA
<213> ORGANISM: Homo sapiens

<400> SEQUENCE: 5
gacatcctga tgacccagtc tccatcctcc ctgtctgcat ctgtaggaga cagagtcacc      60
atcacttgtc gggcgagtca ggatattagc agctggttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
```

```
gaagattttg caacttatta ctgtcaacag tctaatagtt acccgctcac tttcggcgga      300
gggaccaagg tggagatcaa acga                                            324
```

<210> SEQ ID NO 6
<211> LENGTH: 108
<212> TYPE: PRT
<213> ORGANISM: Homo sapiens

<400> SEQUENCE: 6

```
Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Tyr Pro Leu
                85                  90                  95

Thr Phe Gly Gly Gly Thr Lys Val Glu Ile Lys Arg
            100                 105
```

<210> SEQ ID NO 7
<211> LENGTH: 357
<212> TYPE: DNA
<213> ORGANISM: Homo sapiens

<400> SEQUENCE: 7

```
caggtgcagc tggtggagtc ttggggaggc gtggtccagc ctggggaggtc cctgagactc     60 tcctgtgcag cgtctggatt caccttcagt aactatgaca tgtactgggt ccgccaggct    120
ccaggcaagg ggctggagtg ggtggcagtt atattagatg atggaaataa taattactac    180
gcagactccg tgaagggccg attcaccatc tccagagaca attccaagaa aaaggtgtat    240
ctgcaaatga atagcctgag agctgaggac acggctgtgt attactgtgt gagagcgtcc    300
cctaactggg gtcttcttga cttctggggc cagggaaccc tggtcaccgt ctcgagt       357
```

<210> SEQ ID NO 8
<211> LENGTH: 119
<212> TYPE: PRT
<213> ORGANISM: Homo sapiens

<400> SEQUENCE: 8

```
Gln Val Gln Leu Val Glu Ser Trp Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Asp Met Tyr Trp Val Arg Gln Ala Pro Gly Lys Gly Leu Glu Trp Val
        35                  40                  45

Ala Val Ile Leu Asp Asp Gly Asn Asn Tyr Tyr Ala Asp Ser Val
    50                  55                  60

Lys Gly Arg Phe Thr Ile Ser Arg Asp Asn Ser Lys Lys Val Tyr
65                  70                  75                  80

Leu Gln Met Asn Ser Leu Arg Ala Glu Asp Thr Ala Val Tyr Tyr Cys
                85                  90                  95
```

Val Arg Ala Ser Pro Asn Trp Gly Leu Leu Asp Phe Trp Gly Gln Gly
            100                 105                 110

Thr Leu Val Thr Val Ser Ser
            115

<210> SEQ ID NO 9
<211> LENGTH: 324
<212> TYPE: DNA
<213> ORGANISM: Homo sapiens

<400> SEQUENCE: 9
gaaattgtgt tgacacagtc tccatcctca ctgtctgcat ctgtaggaga cagagtcacc    60
atcacttgtc gggcgagtca gggtattagc agctggttag cctggtatca gcagaaacca   120
gggaaagctc ctaagctcct gatctatgat gcctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt acccgatcac cttcggccaa   300
gggacacgac tggagattaa acgt                                          324

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg
            100                 105

<210> SEQ ID NO 11
<211> LENGTH: 357
<212> TYPE: DNA
<213> ORGANISM: Homo sapiens

<400> SEQUENCE: 11
caggtgcagc tggtgcagtc tggggaggc gtggtccagc ctggggaggtc cctgagactc    60 tcctgtgcag cctctggatt catcttcagt agctatgaca tgtactgggt ccgccaggct   120
ccaggcaagg ggctggagtg gtggcagtt atattatatg atggaaataa taaatactac   180
gcagactccg tgaagggccg attcaccatc tccagagaca attccaagaa cacggtgtat   240
ctgcaaatga acagcctgag agctgaggac acggctgtgt attactgtgt gagagcgtcc   300
cctaactggg tcttttttga cttctggggc cagggaaccc tggtcaccgt ctcgagt      357

<210> SEQ ID NO 12
<211> LENGTH: 119
<212> TYPE: PRT
<213> ORGANISM: Homo sapiens -continued

```
<400> SEQUENCE: 12

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Asp Met Tyr Trp Val Arg Gln Ala Pro Gly Lys Gly Leu Glu Trp Val
        35                  40                  45

Ala Val Ile Leu Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Val Arg Ala Ser Pro Asn Trp Gly Leu Phe Asp Phe Trp Gly Gln Gly
            100                 105                 110

Thr Leu Val Thr Val Ser Ser
            115

<210> SEQ ID NO 13
<211> LENGTH: 324
<212> TYPE: DNA
<213> ORGANISM: Homo sapiens

<400> SEQUENCE: 13
gacatccaga tgacccagtc tccatcctcc ctgtctgcat ctgtaggaga cagagtcacc      60
atcacttgcc gggcaagtca gggcattagc agtgatttag cctggtatca gcagaaacca    120
gggaaagctc ctaagctcct gatgtatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt acccgatcac cttcggccaa    300
gggacacgac tggagattaa acgt                                           324

<210> SEQ ID NO 14
<211> LENGTH: 108
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asp
            20                  25                  30

Leu Ala Trp Tyr Gln Gln Lys Pro Gly Lys Ala Pro Lys Leu Leu Met
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg
            100                 105

<210> SEQ ID NO 15
<211> LENGTH: 5
<212> TYPE: PRT
<213> ORGANISM: Homo sapiens
```

```
<400> SEQUENCE: 15

Ser Tyr Ala Ile Ser
1               5

<210> SEQ ID NO 16
<211> LENGTH: 17
<212> TYPE: PRT
<213> ORGANISM: Homo sapiens

<400> SEQUENCE: 16

Gly Ile Ile Pro Leu Phe Asp Thr Thr Lys Tyr Ala Gln Gln Phe Gln
1               5                   10                  15

Gly

<210> SEQ ID NO 17
<211> LENGTH: 19
<212> TYPE: PRT
<213> ORGANISM: Homo sapiens

<400> SEQUENCE: 17

Cys Ala Arg Asp Arg Asp Ile Leu Thr Asp Tyr Tyr Pro Met Gly Gly
1               5                   10                  15

Met Asp Val

<210> SEQ ID NO 18
<211> LENGTH: 5
<212> TYPE: PRT
<213> ORGANISM: Homo sapiens

<400> SEQUENCE: 18

Asn Tyr Asp Met Tyr
1               5

<210> SEQ ID NO 19
<211> LENGTH: 17
<212> TYPE: PRT
<213> ORGANISM: Homo sapiens

<400> SEQUENCE: 19

Val Ile Leu Asp Asp Gly Asn Asn Tyr Tyr Ala Asp Ser Val Lys
1               5                   10                  15

Gly

<210> SEQ ID NO 20
<211> LENGTH: 13
<212> TYPE: PRT
<213> ORGANISM: Homo sapiens

<400> SEQUENCE: 20

Cys Val Arg Ala Ser Pro Asn Trp Gly Leu Leu Asp Phe
1               5                   10

<210> SEQ ID NO 21
<211> LENGTH: 5
<212> TYPE: PRT
<213> ORGANISM: Homo sapiens

<400> SEQUENCE: 21

Ser Tyr Asp Met Tyr
1               5
```

<210> SEQ ID NO 22
<211> LENGTH: 17
<212> TYPE: PRT
<213> ORGANISM: Homo sapiens

<400> SEQUENCE: 22

Val Ile Leu Tyr Asp Gly Asn Asn Lys Tyr Tyr Ala Asp Ser Val Lys
1               5                   10                  15
Gly

<210> SEQ ID NO 23
<211> LENGTH: 13
<212> TYPE: PRT
<213> ORGANISM: Homo sapiens

<400> SEQUENCE: 23

Cys Val Arg Ala Ser Pro Asn Trp Gly Leu Phe Asp Phe
1               5                   10

<210> SEQ ID NO 24
<211> LENGTH: 11
<212> TYPE: PRT
<213> ORGANISM: Homo sapiens

<400> SEQUENCE: 24

Arg Ala Ser Gln Gly Ile Ser Ser Val Leu Ala
1               5                   10

<210> SEQ ID NO 25
<211> LENGTH: 7
<212> TYPE: PRT
<213> ORGANISM: Homo sapiens

<400> SEQUENCE: 25

Asp Ala Ser Ser Leu Glu Ser
1               5

<210> SEQ ID NO 26
<211> LENGTH: 9
<212> TYPE: PRT
<213> ORGANISM: Homo sapiens

<400> SEQUENCE: 26

Gln Gln Ser Asn Ser Tyr Pro Leu Thr
1               5

<210> SEQ ID NO 27
<211> LENGTH: 9
<212> TYPE: PRT
<213> ORGANISM: Homo sapiens

<400> SEQUENCE: 27

Gln Gln Ser Asn Ser Tyr Pro Leu Thr
1               5

<210> SEQ ID NO 28
<211> LENGTH: 11
<212> TYPE: PRT
<213> ORGANISM: Homo sapiens

<400> SEQUENCE: 28

Arg Ala Ser Gln Asp Ile Ser Ser Trp Leu Ala
1               5                   10

```
<210> SEQ ID NO 29
<211> LENGTH: 9
<212> TYPE: PRT
<213> ORGANISM: Homo sapiens

<400> SEQUENCE: 29

Gln Gln Ser Asn Ser Tyr Pro Ile Thr
1               5

<210> SEQ ID NO 30
<211> LENGTH: 11
<212> TYPE: PRT
<213> ORGANISM: Homo sapiens

<400> SEQUENCE: 30

Arg Ala Ser Gln Gly Ile Ser Ser Val Asp Ala
1               5                   10

<210> SEQ ID NO 31
<211> LENGTH: 9
<212> TYPE: PRT
<213> ORGANISM: Homo sapiens

<400> SEQUENCE: 31

Gln Gln Ser Asn Ser Tyr Pro Ile Thr
1               5

<210> SEQ ID NO 32
<211> LENGTH: 9
<212> TYPE: PRT
<213> ORGANISM: Homo sapiens

<400> SEQUENCE: 32

Gln Gln Ser Gln Ser Tyr Pro Leu Thr
1               5

<210> SEQ ID NO 33
<211> LENGTH: 17
<212> TYPE: PRT
<213> ORGANISM: Homo sapiens

<400> SEQUENCE: 33

Gly Ile Ile Pro Leu Phe Asp Thr Thr Lys Tyr Ala Gln Lys Phe Gln
1               5                   10                  15

Gly

<210> SEQ ID NO 34
<211> LENGTH: 17
<212> TYPE: PRT
<213> ORGANISM: Homo sapiens

<400> SEQUENCE: 34

Gly Ile Ile Pro Ala Phe Glu Thr Thr Lys Tyr Ala Gln Lys Phe Gln
1               5                   10                  15

Gly

<210> SEQ ID NO 35
<211> LENGTH: 17
<212> TYPE: PRT
<213> ORGANISM: Homo sapiens
```

<400> SEQUENCE: 35

Gly Ile Ile Pro Ala Phe Asp Thr Thr Lys Tyr Ala Gln Lys Phe Gln
1               5                   10                  15
Gly

<210> SEQ ID NO 36
<211> LENGTH: 16
<212> TYPE: PRT
<213> ORGANISM: Homo sapiens

<400> SEQUENCE: 36

Asp Arg Asp Ile Leu Thr Asp Tyr Tyr Pro Met Gly Gly Met Asp Val
1               5                   10                  15

<210> SEQ ID NO 37
<211> LENGTH: 16
<212> TYPE: PRT
<213> ORGANISM: Homo sapiens

<400> SEQUENCE: 37

Asp Arg Asp Ile Leu Thr Asp Tyr Tyr Pro Leu Gly Gly Met Asp Val
1               5                   10                  15

<210> SEQ ID NO 38
<211> LENGTH: 8
<212> TYPE: PRT
<213> ORGANISM: Homo sapiens

<400> SEQUENCE: 38

Thr Ala Val Phe Tyr Cys Ala Arg
1               5

<210> SEQ ID NO 39
<211> LENGTH: 8
<212> TYPE: PRT
<213> ORGANISM: Homo sapiens

<400> SEQUENCE: 39

Thr Ala Val Tyr Tyr Cys Ala Arg
1               5

<210> SEQ ID NO 40
<211> LENGTH: 142
<212> TYPE: PRT
<213> ORGANISM: Homo sapiens

<400> SEQUENCE: 40

Gln Gly Cys Gly Ile Leu Gln Pro Asp Pro Ala Asn Ile Thr Val
1               5                   10                  15

Thr Ala Val Ala Arg Asn Pro Arg Trp Leu Ser Val Thr Trp Gln Asp
                20                  25                  30

Pro His Ser Trp Asn Ser Ser Phe Tyr Arg Leu Arg Phe Glu Leu Arg
                35                  40                  45

Tyr Arg Ala Glu Arg Ser Lys Thr Phe Thr Thr Trp Met Val Lys Asp
            50                  55                  60

Leu Gln His His Cys Val Ile His Asp Ala Trp Ser Gly Leu Arg His
65                  70                  75                  80

Val Val Gln Leu Arg Ala Gln Glu Phe Gly Gln Gly Glu Trp Ser
                85                  90                  95

Glu Trp Ser Pro Glu Ala Met Gly Thr Pro Trp Thr Glu Ser Arg Ser
                100                 105                 110

```
Pro Pro Ala Glu Asn Glu Val Ser Thr Pro Met Gln Ala Leu Thr Thr
        115                 120                 125

Asn Lys Asp Asp Asp Asn Ile Leu Phe Arg Asp Ser Ala Asn
        130                 135                 140

<210> SEQ ID NO 41
<211> LENGTH: 143
<212> TYPE: PRT
<213> ORGANISM: Mus musculus

<400> SEQUENCE: 41

His Ser Leu Lys Met Val Gln Pro Asp Pro Ala Asn Leu Val Val
1               5                   10                  15

Ser Ala Ile Pro Gly Arg Pro Arg Trp Leu Lys Val Ser Trp Gln His
            20                  25                  30

Pro Glu Thr Trp Asp Pro Ser Tyr Tyr Leu Leu Gln Phe Gln Leu Arg
            35                  40                  45

Tyr Arg Pro Val Trp Ser Lys Glu Phe Thr Val Leu Leu Pro Val
50                  55                  60

Ala Gln Tyr Gln Cys Val Ile His Asp Ala Leu Arg Gly Val Lys His
65                  70                  75                  80

Val Val Gln Val Arg Gly Lys Glu Glu Leu Asp Leu Gly Gln Trp Ser
                85                  90                  95

Glu Trp Ser Pro Glu Val Thr Gly Thr Pro Trp Ile Ala Glu Pro Arg
                100                 105                 110

Thr Thr Pro Ala Gly Ile Leu Trp Asn Pro Thr Gln Val Ser Val Glu
            115                 120                 125

Asp Ser Ala Asn His Glu Asp Gln Tyr Glu Ser Thr Glu Ala
        130                 135                 140

<210> SEQ ID NO 42
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is N or Q

<400> SEQUENCE: 42

Gln Gln Ser Xaa Ser Tyr Pro Leu Thr
1               5

<210> SEQ ID NO 43
<211> LENGTH: 17
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X is L or A
<220> FEATURE:
<221> NAME/KEY: MISC_FEATURE
<222> LOCATION: (7)..(7)
<223> OTHER INFORMATION: X is D or E
<220> FEATURE:
<221> NAME/KEY: MISC_FEATURE
<222> LOCATION: (14)..(14)
<223> OTHER INFORMATION: X is Q or K

<400> SEQUENCE: 43

Gly Ile Ile Pro Xaa Phe Xaa Thr Thr Lys Tyr Ala Gln Xaa Phe Gln
1               5                   10                  15

Gly
```

```
<210> SEQ ID NO 44
<211> LENGTH: 16
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: X is M or L

<400> SEQUENCE: 44

Asp Arg Asp Ile Leu Thr Asp Tyr Tyr Pro Xaa Gly Gly Met Asp Val
1               5                   10                  15

<210> SEQ ID NO 45
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X is F or Y

<400> SEQUENCE: 45

Thr Ala Val Xaa Tyr Cys Ala Arg
1               5

<210> SEQ ID NO 46
<211> LENGTH: 6
<212> TYPE: PRT
<213> ORGANISM: Homo sapiens

<400> SEQUENCE: 46

Ala Glu Arg Ser Lys Thr
1               5
```